(12) United States Patent
Salas Falgueras et al.

(10) Patent No.: US 8,404,808 B2
(45) Date of Patent: Mar. 26, 2013

(54) PHAGE PHI29 DNA POLYMERASE CHIMERA

(75) Inventors: Margarita Salas Falgueras, Madrid (ES); Miguel De Vega Jose, Madrid (ES); Jose M. Lazaro Bolos, Madrid (ES); Luis Blanco Davila, Madrid (ES); Mario Mencia Caballero, Madrid (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 0 days.

(21) Appl. No.: 13/381,837

(22) PCT Filed: Jul. 1, 2010

(86) PCT No.: PCT/ES2010/070454
§ 371 (c)(1),
(2), (4) Date: Mar. 21, 2012

(87) PCT Pub. No.: WO2011/000997
PCT Pub. Date: Jan. 6, 2011

(65) Prior Publication Data
US 2012/0190014 A1     Jul. 26, 2012

(30) Foreign Application Priority Data
Jul. 2, 2009    (ES) .................................. 200930413

(51) Int. Cl.
*C07K 1/00*    (2006.01)
*C12N 9/00*    (2006.01)

(52) U.S. Cl. ...................................... 530/350; 435/183
(58) Field of Classification Search ........................ None
See application file for complete search history.

(56) References Cited

FOREIGN PATENT DOCUMENTS
WO      2004013279 A2    2/2004

OTHER PUBLICATIONS

Pavlov, A.R., Belova, G.I., Konzyavkins, S.A., Slesarev, A.I. Helix-hairpin-helix motifs confers salt resistance and processivity on chimeric DNA polymerases. Proceedings of the National Academy of Sciences of the United States of America. Oct. 2002, vol. 99 No. 21, paginas 13510-13515, ISSN 0027-8424.<Doi:10.1073/pnas.202127199>.

Rodriguez, I., Lazaro, J.M., Blanco, L. et al. A specific subdomain in Phi29 DNA polymerase confers both processivity and strand displacement capacity. Proceedings of the National Academy of Sciences of the United of States, May 2005, vol. 102, No. 18, paginas 6407-6412. ISSN 0027-8424.<Doi:10.1073/pnas.0500597102>.

Kamtekar, S., Berman, A.J., Wang, J. et al. Insights into strand displacement and processivity from the crystal structure of protein-primed DNA polymerase of bacteriophage Phi29, Molecular Cell. Nov. 2004, vol. 16 No. 4 paginas 609-618. ISSN 1097-2765.<Doi:10.1016/j.molce1.2004.10.019>.

Blasco, M.A. Blanco, L., Pares, E., et al. Structural and funtional analysis of temperature-sensitive mutants of the phage Phi29 DNA polymerase, Nucleic Acids Research. Agosto 1990, vol. 18, No. 16, paginas 4763-4770. ISSN 0305-1048. & Base de datos UniProt. Numero de acceso Q38545, Version 44. [en linea] 16.12.2008 [recuperado el 19.10.2010] Recuperado de Internet<URL:http://www.ebi.ac.uk/uniprot/unisave/?help+0&session=/ebi/extserv/old-work/SESSION23172-1287478337-1&index=8&view=623276632&issue_date=Dec. 16, 2008>.

Blanco, L., Prieto, I., Gutierrez, J. et al. Effect of NH4+ions on Phi29 DNA-proteins p3 replication: formation of a complex between the terminal protein and the DNA polymerase. Journal of Virology. Dec. 1987, vol. 61, No. 12, paginas 3983-3991.ISSN 0022-538X.

*Primary Examiner* — Suzanne M Noakes
*Assistant Examiner* — Jae W Lee
(74) *Attorney, Agent, or Firm* — Sullivan & Worcester LLP; Christopher T. McWhinney

(57) ABSTRACT

A DNA polymerase chimera comprising an amino-terminal (N-terminal) region encoding a Φ29 type DNA polymerase and a carboxyl-terminal (C-terminal) region comprising at least one HhH domain which are bound by a connecting amino acid sequence is disclosed along with and the use thereof for replicating, amplifying or sequencing a template DNA. Also disclosed is a method for replicating, amplifying or sequencing a deoxyribonucleic acid with the DNA polymerase chimera and kits for carrying out the methods.

17 Claims, 8 Drawing Sheets

PHAGE PHI29 DNA POLYMERASE CHIMERA

SEQUENCE LISTING

The instant application contains a Sequence Listing which has been submitted via EFS-Web as an ASCII text file and is hereby incorporated by reference in its entirety. Said ASCII file, created on Nov. 6, 2012, is named Substitute-SEQ22328_0011US.txt and is 17,577 bytes in size.

CROSS REFERENCE TO RELATED APPLICATIONS

This application is a national stage of International Application No. PCT/ES2010/070454, filed Jul. 1, 2010, which claims priority under 35 U.S.C. §119 to Spanish Patent Application No. P 200930413, filed Jul. 2, 2009, the entire disclosure of which is herein expressly incorporated by reference.

FIELD OF THE INVENTION

The present invention is encompassed within the biotechnology field. Specifically, it relates to a DNA polymerase chimera comprising an amino-terminal (N-terminal) region encoding a φ29 type DNA polymerase and a carboxyl-terminal (C-terminal) region comprising at least one HhH domain which are bound by means of a connecting amino acid sequence and to the use thereof for replicating, amplifying or sequencing a template DNA. Likewise, the present invention provides a method for replicating, amplifying or sequencing a deoxyribonucleic acid with said DNA polymerase chimera and a kit for carrying out said method.

BACKGROUND AND SUMMARY

The only enzyme required by the bacteriophage φ29 to replicate its genome is its DNA polymerase, a 66 KDa monomeric protein capable of catalyzing both the initiation of the replication and the elongation of the synthesized strand. For the initiation, this polymerase is bound to a protein known as "terminal" (TP), recognizes the end of the φ29 DNA and catalyzes the formation of a TP-dAMP covalent complex. After the polymerization of 10 nucleotides, the DNA polymerase/TP heterodimer disassociates and the elongation of the strand coming from DNA is carried out.

Replicative DNA polymerases require the interaction with accessory proteins which stabilize the binding between the enzyme and the DNA (Kuriyan and O'Donnell. J Mol Biol. 1993; 234: 915-925). On the other hand, said DNA polymerases need to couple the polymerization upon the detachment of the DNA strand which is not being copied for which they require the functional association thereof to helicase type proteins. In this sense, the DNA polymerase of the bacteriophage φ29 has various intrinsic functional characteristics making it unique:

a) High processivity (defined as the number of nucleotides incorporated by binding event).
b) High strand detachment capacity which allows replicating the genome of said bacteriophage in the absence of helicase type accessory proteins. These two characteristics, processivity and strand detachment allow the φ29 DNA polymerase to be capable of synthesizing DNA strands of more than 70 kb in length (Blanco et al. J Biol Chem. 1989; 264: 8935-8940).
c) High accuracy in the insertion of nucleotides in the new strand (Esteban et al. J Biol Chem. 1993; 268: 2719-2726).

All these characteristics have led to the development of a great variety of isothermal process (at constant temperature) protocols for amplifying double stranded DNA (dsDNA) based on the use of this polymerase. In a simple configuration, the capacity of the φ29 DNA polymerase to use circular single stranded DNA (ssDNA) allows amplifying DNA by the rolling circle method (or RCA—rolling-circle amplification), producing ssDNA molecules of great length and containing more than 10 copies of the circular template (Blanco et al. J Biol Chem. 1989; 264: 8935-8940; U.S. Pat. No. 5,001,050, U.S. Pat. No. 5,198,543 and U.S. Pat. No. 5,576,204). In the process for amplifying dsDNA developed by Amersham Biosciences/Molecular Staging (Dean et al. Genome Res. 2001; 11: 1095-1099; Dean et al. Proc Natl Acad Sci USA. 2002; 99: 5261-5266), the combination of the use of the φ29 DNA polymerase with the use of hexamers (hexa-nucleotides) random sequence primers allows obtaining amplification factors of $10^4$-$10^6$ starting from picograms of circular plasmid DNA [Templiphi™ of GE Healthcare] or from 10 nanograms of Genomic DNA [Genomiphi™ of GE Healthcare and Repli-G® of Qiagen]. The products produced are of high quality and can be digested or sequenced directly without the need of prior purification, it has been demonstrated that the φ29 DNA polymerase is the most robust enzyme for this purpose. The common buffer for carrying out the amplification reactions with the φ29 DNA polymerase contains tris-HCl (pH 7.5) plus different concentrations (in the millimolar order) of NaCl or KCl and $MgCl_2$ (US20030207267). However, in spite of the satisfactoriness of these protocols in very diverse situations, the development of other protocols which allow starting from lesser DNA amounts is a growing need.

The HhH ("helix-hairpin-helix") motifs bind the DNA regardless of its sequence and are found in various DNA polymerases, ligases and glycosylases (Shao and Grishin. Nucleic Acids Res. 2000; 28: 2643-2650; Doherty et al. Nucleic Acids Res. 1996; 24:2488-2497). These motifs contain a pair of anti-parallel α-helixes connected by a "hairpin" type loop. The second α-helix does not protrude from the structure and therefore, unlike other DNA binding motifs, it cannot be intercalated in the major groove of the DNA. Crystallographic studies suggest that the protein-DNA interactions are established through the "loop" between the two α-helices. This loop is involved in establishing nonspecific interactions with the DNA and normally contains the consensus sequence GhG, wherein h is a hydrophobic residue normally I, V, or L. The resolution of crystallographic structures suggests that the interactions are established between the nitrogen of the polypeptide strand and the oxygen of the phosphates of the DNA. Furthermore, polar amino acids which would establish additional interactions with the phosphate groups tend to exist in the positions 2 and 3 with respect to the second G. The last G of the consensus sequence forms the N-terminal part of the second α-helix and the hydrophobic residue h contributes to the interactions between the two α-helices of the motif. The two α-helices are packaged forming an angle of 25-50° between one another dictating the characteristic hydrophobic pattern in the sequences. The HhH motifs generally form part of major structures known as $(HhH)_2$ made up by two HhH motifs bound by an α-helix, forming a mirror symmetry with respect to that of the DNA facilitating the stable binding thereof to the same (Shao and Grishin. Nucleic Acids Res. 2000; 28: 2643-2650; Doherty et al. Nucleic Acids Res. 1996; 24:2488-2497; Thayer et al. EMBO J. 1995; 14: 4108-4120).

The formation of chimeras between heat stable DNA polymerases such as Taq and Pfu and nonspecific DNA binding motifs has been previously used to increase the DNA binding capacity by said polymerases. (Pavlov et al. Proc Natl Acad Sci USA. 2002; 99: 13510-13515; WO2004013279; Wang et al. Nucleic Acids Res. 2004; 32: 1197-1207).

The crystallographic resolution of the structure of the φ29 DNA polymerase has provided the molecular bases responsible for the processive polymerization coupled to the strand detachment, a specific characteristic of this enzyme (Kamtekar et al. 2006; EMBO J 25: 1335-1343).

The comparative analysis with other DNA polymerases of the eukaryotic type (family B) shows a similar general folding: a C-terminal polymerization domain formed by the universal subdomains fingers, palm and thumb and forming a channel through which the DNA is bound; and a 3"-5" N-terminal exonuclease domain responsible for removing the nucleotides mistakenly incorporated during the polymerization. The main structural difference between the DNA polymerases of known structure and that of φ29 is the presence, in the latter, of two additional subdomains in its polymerization domain, both corresponding to insertions of conserved sequence in the subgroup of the DNA polymerases using a protein called TPR1 and TPR2 as primer. The subdomain TPR1 is located close to palm and contacts with the DNA duplex. The subdomain TPR2, with a β-hairpin structure forms, close to the subdomains thumb, palm and fingers, an annular structure which would completely surround the newly synthesized DNA, binding the DNA polymerase to the DNA, required for replicating in a processive manner. Likewise, the subdomain TPR2, together with the subdomains fingers, palm and the exonuclease domain, participates in the formation of a narrow channel through which the template strand passes to access the active center during replication, forcing the separation of the double stranded DNA as the polymerase is displaced, acting in a manner similar to how a helicase would act and providing the polymerase with its capacity of coupling the polymerization to the strand detachment (Kamtekar et al. 2006; EMBO J 25: 1335-1343; Rodriguez et al. 2005; Proc Natl Acad Sci USA 102: 6407-6412). Such significant differences in the polymerization domain of the φ29 DNA polymerase with respect to the rest has the effect that the fusion of a peptide in the C-terminal end thereof would have unpredictable binding properties thereof in the polymerization and DNA.

BRIEF DESCRIPTION OF THE DRAWINGS

Features and advantages of the present invention will become apparent to those skilled in the art from the following description with reference to the drawings, in which.

DETAILED DESCRIPTION

Figure 1:
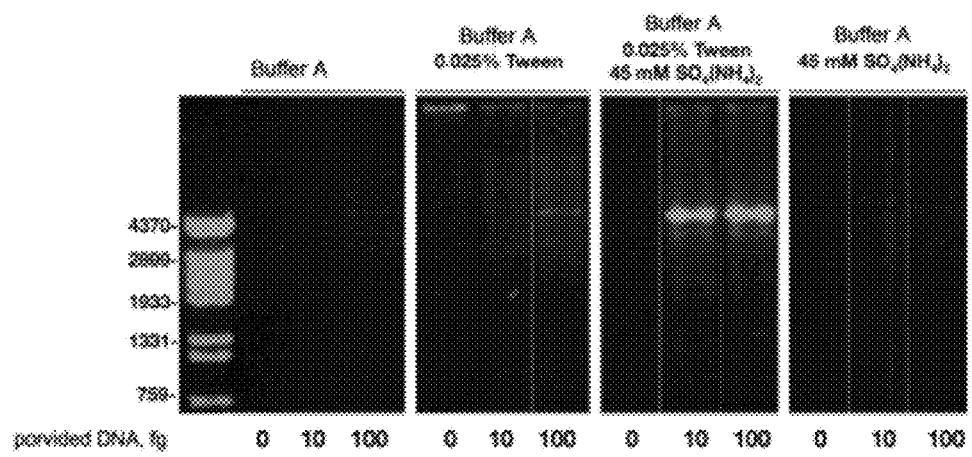
FIG. 1 shows the effect of Tween® 20 and (NH4)2SO4 in the amplification capacity of the φ29 DNA polymerase. The assay was carried out as described in the main text in the presence of the indicated amounts of plasmid DNA (4.2 kpb). After incubating at 30° C. for 5 h, the reactions were analyzed as described in the main text. On the left, the linear DNA fragments obtained after digesting the φ29 DNA with HindIII used as DNA length markers.

For simplicity and illustrative purposes, the principles of the present invention are described by referring to various examples. One of ordinary skill in the art will readily recognize that the same principles are equally applicable to, and can be implemented in other forms, and that any such variation would be within those modifications that do not part from the true spirit and scope of the present invention. The invention is not limited in its application to the details of any particular formulation shown, since the invention is capable of other embodiments. The following examples are provided for illustrative purposes and do not and should not be understood to limit the claims appended hereto. The terminology used herein is for the purpose of description and not of limitation.

The present invention relates to a DNA polymerase chimera comprising a N-terminal region encoding a φ29 type DNA polymerase and a C-terminal region comprising, at least one HhH domain which are bound by means of a connecting amino acid sequence and to the use thereof for replicating, amplifying or sequencing a template DNA. Likewise, the present invention provides a method for replicating, amplifying or sequencing a deoxyribonucleic acid with said DNA polymerase chimera and a kit for carrying out said method.

The phage φ29 DNA polymerase has several characteristics of great interest for amplifying DNA such as: a high processivity without the need of the participation of any accessory protein and a high strand detachment capacity allowing it to replicate the genome of said bacteriophage in a single binding event to the DNA, as well as a high accuracy in the insertion of nucleotides in the new strand. These characteristics have lead to the development of a great variety of protocols for the isothermal amplification of DNA based on the use of this polymerase which allow obtaining products of high quality that can be digested or sequenced directly without the need of prior purification. However, there is a need for protocols which allow the amplification of DNA from lesser amounts thereof. The present invention responds to this need by means of two approaches: 1) the development of a composition which significantly improves the specificity and the yield of the reaction, and 2) the formation of chimeras between the φ29 DNA polymerase and nonspecific DNA binding motifs increasing the DNA binding capacity of the enzyme.

In the examples of this patent, it is shown that the simultaneous addition of polyoxyethylenated sorbitan monolaurate (Tween®20) and an ammonium salt to the buffer commonly used for the amplification with the φ29 DNA polymerase, on the one hand, prevents the non-specific DNA amplification and, on the other hand allows the detectable and specific amplification from limiting amounts of 0.1 femtograms (fg) of plasmid DNA and 10 fg of genomic DNA as template.

With respect to the increase of the DNA binding capacity, in the present invention HhH motifs of the topoisomerase V of *Methanopyrus kandleri* have been fused to the carboxyl end of the φ29 DNA polymerase through a connecting sequence or linker originating from 4 different chimeras. These chimeras are capable of amplifying the template DNA from an amount less than that required by the natural φ29 DNA polymerase.

A first aspect of the present invention relates to a DNA polymerase chimera (hereinafter, DNA polymerase chimera of the invention) comprising:
a) an amino acid sequence encoding a φ29 type DNA polymerase bound by its C-terminal end to
b) a connecting amino acid sequence bound by its C-terminal end to
c) an amino acid sequence comprising at least one helix-hairpin-helix domain (HhH).

As used in the present description, the term "DNA polymerase" relates to an enzyme capable of catalyzing the polymerization of deoxynucleoside triphosphates. Generally, the enzyme initiates the synthesis in the 3' end of a primer hybridized with a template DNA sequence and proceeds towards the 5' end of the template DNA strand.

As used in the present description, the term "chimera" relates to a protein, the amino acid sequence of which is a product of fusion of amino acid sequences of at least two different proteins. A chimeric protein is generally produced by means of its expression from a chimeric DNA encoding the chimeric amino acid sequence.

As used in the present description, the terms "DNA polymerase chimera" or "chimeric DNA polymerase" relate to a protein, the amino acid sequence of which is a product of fusion of amino acid sequences of at least two different proteins, of which one is a DNA polymerase, and which is capable of catalyzing the polymerization of deoxynucleoside triphosphates. The DNA polymerase chimera of the invention comprises an N-terminal region encoding a φ29 type DNA polymerase (a), and a C-terminal region comprising at least one HhH domain (c) which are bound by means of a connecting amino acid sequence (b).

As used in the present invention, the term "φ29 type DNA polymerase" relates to any DNA polymerase containing TPR1 and TPR2 subdomains in its polymerization domain providing the polymerase with the capacity of coupling the processive polymerization to the strand detachment. Examples of φ29 type DNA polymerases that can be used in the present invention are selected from the list comprising the DNA polymerases isolated from the following phages: φ29, Cp-1, PRD-1, φ15, φ21, PZE, PZA, Nf, M2Y, B103, GA-1, SF5, Cp-5, Cp-7, PR4, PR5, PR722, L17 or *Acidianus* Bottle-shaped virus (ABV).

In a preferred embodiment of this first aspect of the invention, the amino acid sequence of (a) of the DNA polymerase chimera of the invention encodes a φ29 type DNA polymerase which is selected from the DNA polymerases isolated from the following phages: φ29, Cp-1, PRD-1, φ15, φ21, PZE, PZA, Nf, M2Y, B103, GA-1, SF5, Cp-5, Cp-7, PR4, PR5, PR722, L17 or *Acidianus* Bottle-shaped virus (ABV).

Preferably, the amino acid sequence of (a) of the DNA polymerase chimera of the invention has a identity of at least 80% with SEQ ID NO: 1. More preferably, the amino acid sequence of (a) of the chimera of the invention has an identity of at least 90% with SEQ ID NO: 1. Still more preferably, the amino acid sequence of (a) of the chimera of the invention is SEQ ID NO: 1.

The exonuclease domain of the φ29 type DNA polymerases is known and can be modified to reduce the exonuclease activity retaining a high processivity and strand detachment capacity. These modified DNA polymerases are especially useful for sequencing large molecules.

In a preferred embodiment of this first aspect of the invention, the amino acid sequence of (a) of the DNA polymerase chimera of the invention encodes a φ29 type DNA polymerase having modification in the exonuclease domain, wherein said modified DNA polymerase has preferably, less than 10% of exonuclease activity and, more preferably, less than 1% of exonuclease activity than the corresponding naturally occurring DNA polymerase or "wild type". In a still more preferred embodiment, said modified φ29 type DNA polymerase lacks detectable exonuclease activity with respect to the corresponding naturally occurring DNA polymerase.

The HhH ("helix-hairpin-helix") motifs are non-sequence dependent DNA binding motifs. Structurally, the HhH motifs are formed by a pair of anti-parallel α-helixes connected by a hook-type loop. This loop is involved in the interaction with the DNA and has in general a consensus sequence consisting of glycine-amino acid hydrophobic-glycine (GhG) wherein h is a hydrophobic amino acid residue, commonly, leucine, isoleucine or valine. The last glycine of the consensus sequence serves as N-terminal residue of the second α-helix and the hydrophobic residue h contributes to the interactions between the two α-helixes of the motif.

Examples of proteins having a HhH motif in their sequence are, but not limited to, the DNA topoisomerase V of *Methanopyrus kandleri*, the proteins MutY, Nth, MutM/Fpg, Nei, UvrC, DinP, RecR, UmuC, DnaE or DnlJ of *Escherichia coli* or the proteins RAD1, RAD2, RAD10, RAD27, RAD 55, RAD 57, REV1, OGG1, NTG1, NTG2, DIN-7 or EXO-1 of yeasts, as well as the homologs of these proteins in other organisms such as for example, but not limited to, *Bacillus subtilis, Caenorhabditis elegans, Haemophilus influenzae, Methanococcus jannaschii, Micrococcus luteus, Methanobacterium thermoformicum* or *Salmonella typhimurium*.

Therefore, in a preferred embodiment of this first aspect of the invention, the amino acid sequence of (c) of the DNA polymerase chimera of the invention comprises at least one HhH domain of a protein which is selected from the list comprising:

topoisomerase V of *M. kandleri*,

MutY, Nth, MutM/Fpg, Nei, UvrC, DinP, RecR, UmuC, DnaE or DnlJ of *E. coli*,

RAD1, RAD2, RAD10, RAD27, RAD 55, RAD 57, REV1, OGG1, NTG1, NTG2, DIN-7 or EXO-1 of yeasts, or a homologous protein of the above in *B. subtilis, C. elegans, H. influenzae, M. jannaschii, M. luteus, M. thermoformicum* or *S. typhimurium*.

The C-terminal end of the topoisomerase V of *M. kandler* is organized into 12 repeats of about 50 amino acids each known as A-L domains and each having two HhH motifs.

In a preferred embodiment of this first aspect of the invention, the amino acid sequence of (c) of the DNA polymerase chimera of the invention, comprises at least one HhH domain derived from the topoisomerase V of *M. kandleri*, the amino acid sequence of which is SEQ ID NO: 2.

In a more preferred embodiment of this first aspect of the invention, the amino acid sequence of (c) of the DNA polymerase chimera of the invention is SEQ ID NO: 3 corresponding to the sequence of the H domain of the topoisomerase V of *M. kandleri*.

In another more preferred embodiment of this first aspect of the invention, the amino acid sequence of (c) of the DNA polymerase chimera of the invention is SEQ ID NO: 3 bound by its C-terminal end to SEQ ID NO: 4 corresponding to the sequence of the H domain of the topoisomerase V of *M. kandleri* bound by its C-terminal end to the I domain of the topoisomerase V of *M. kandleri*.

As used in the present invention, the term "connecting amino acid sequence" relates to a short amino acid sequence of at least 2 amino acids in length which allows maintaining the functionality of the amino acid sequences of (a) and (c) of the DNA polymerase chimera of the invention. Preferably, the connecting amino acid sequence of (b) is of 6 amino acids. More preferably, the connecting amino acid sequence of (b) is SEQ ID NO: 5 or SEQ ID NO: 6.

Another aspect of the present invention relates to the use of the DNA polymerase chimera of the invention for replicating, amplifying or sequencing a template DNA.

Another aspect of the present invention relates to a method for replicating, amplifying or sequencing a template DNA which comprises contacting said DNA with a reaction mixture comprising at least:

a) the DNA polymerase chimera of the invention,
b) a buffer,
c) magnesium chloride,
d) a primer, and
e) nucleoside triphosphates.

A preferred embodiment of this aspect of the invention relates to a method for replicating, amplifying or sequencing a template DNA which comprises contacting said DNA with a reaction mixture comprising the aforementioned elements (a)-(e) and further comprising polyoxyethylenated sorbitan monolaurate, an ammonium salt, a potassium salt or a combination of any of the above.

In a preferred embodiment of the method for replicating, amplifying or sequencing of the invention, the DNA polymerase chimera of the invention is at a concentration between 5 nM and 75 nM. In a more preferred embodiment, the DNA polymerase chimera of the invention is at a concentration between 25 nM and 60 nM. In a still more preferred embodiment, the DNA polymerase chimera of the invention is at a concentration of approximately 50 nM.

In a preferred embodiment of the method for replicating, amplifying or sequencing of the invention, the polyoxyethylenated sorbitan monolaurate (Tween® 20) is at a concentration between 0.003% and 0.1% of the total volume of the reaction. In a more preferred embodiment, the polyoxyethylenated sorbitan monolaurate is in a proportion between 0.006% and 0.05% of the total volume of the reaction. In a still more preferred embodiment, the polyoxyethylenated sorbitan monolaurate is in a proportion between 0.01% and 0.03% of the total volume of the reaction. In a still more preferred embodiment, the polyoxyethylenated sorbitan monolaurate is in a proportion of approximately 0.025% of the total volume of the reaction. "Total volume of the reaction", is understood as the resulting volume after the addition of the template DNA to the reaction mixture.

In a preferred embodiment of the method for replicating, amplifying or sequencing of the invention, the ammonium salt is selected from the list comprising: ammonium sulfate, ammonium chloride or ammonium acetate.

In a preferred embodiment of the method for replicating, amplifying or sequencing of the invention, the ammonium salt is ammonium sulfate. In a more preferred embodiment, the ammonium sulfate is at a concentration between 30 mM and 60 mM. In a still more preferred embodiment, the ammonium sulfate is at a concentration between 40 mM and 50 mM. In a still more preferred embodiment, the ammonium sulfate is at a concentration of approximately 45 mM.

In a preferred embodiment of the method for replicating, amplifying or sequencing of the invention, the ammonium salt is ammonium chloride. In a more preferred embodiment, the ammonium chloride is at a concentration between 60 mM and 120 mM. In a still more preferred embodiment, the ammonium chloride is at a concentration between 80 mM and 100 mM. In a still more preferred embodiment, the ammonium chloride is at a concentration of approximately 90 mM.

In a preferred embodiment of the method for replicating, amplifying or sequencing of the invention, the ammonium salt is ammonium acetate. In a more preferred embodiment, the ammonium acetate is at a concentration between 60 mM and 120 mM. In a still more preferred embodiment, the ammonium acetate is at a concentration between 80 mM and 100 mM. In a still more preferred embodiment, the ammonium acetate is at a concentration of approximately 90 mM.

In a preferred embodiment of the method for replicating, amplifying or sequencing of the invention, the buffer is at a pH between 7.0 and 8.5. In a more preferred embodiment, the buffer is at a pH between 7.2 and 8. In a still more preferred embodiment, the buffer is at a pH of approximately 7.5.

In a preferred embodiment of the method for replicating, amplifying or sequencing of the invention, the buffer is tris-hydrochloric, tris-acetic or HEPES. In a more preferred embodiment of the method for replicating, amplifying or sequencing of the invention, the buffer tris-hydrochloric, tris-acetic or HEPES is at a pH between 7.0 and 8.5. In a still more preferred embodiment, the buffer tris-hydrochloric, tris-acetic or HEPES is at a pH between 7.2 and 8. In a still more preferred embodiment, the buffer tris-hydrochloric, tris-acetic or HEPES is at a pH of approximately 7.5.

In a preferred embodiment of this aspect of the method for replicating, amplifying or sequencing of the invention, the buffer tris-hydrochloric, tris-acetic or HEPES is at a concentration between 25 mM and 50 mM. In a more preferred embodiment, the buffer tris-hydrochloric, tris-acetic or HEPES is at a concentration between 30 mM and 45 mM. In a still more preferred embodiment, the buffer tris-hydrochloric, tris-acetic or HEPES is at a concentration of approximately 40 mM.

In a preferred embodiment of the method for replicating, amplifying or sequencing of the invention, the potassium salt is potassium chloride or potassium acetate. In a more preferred embodiment, the potassium chloride or the potassium acetate is at a concentration between 30 mM and 70 mM. In a still more preferred embodiment, the potassium chloride or the potassium acetate is at a concentration between 40 mM and 60 mM. In a still more preferred embodiment, the potassium chloride or the potassium acetate is at a concentration of approximately 50 mM.

In a preferred embodiment of the method for replicating, amplifying or sequencing of the invention, the magnesium chloride is at a concentration between 2 mM and 20 mM. In a more preferred embodiment, the magnesium chloride is at a concentration between 5 mM and 15 mM. In a still more preferred embodiment, the magnesium chloride is at approximately 10 mM.

In a preferred embodiment of the method for replicating, amplifying or sequencing of the invention, the polyoxyethylenated sorbitan monolaurate is in a proportion between 0.01% and 0.03% of the total volume, the ammonium sulfate is at a concentration between 40 mM and 50 mM, the buffer tris-hydrochloric, tris-acetic or HEPES is at a concentration between 30 mM and 45 mM and at a pH between 7.2 and 8.0, the magnesium chloride is at a concentration between 5 mM and 15 mM and the potassium chloride or the potassium acetate is at a concentration between 40 mM and 60 mM.

In a preferred embodiment of the method for replicating, amplifying or sequencing of the invention, the polyoxyethylenated sorbitan monolaurate is in a concentration of 0.025% of the total volume, the ammonium sulfate is at a concentration of 45 mM, the buffer tris-hydrochloric, tris-acetic or HEPES is at a concentration of 40 mM and at a pH of 7.5, the magnesium chloride is at a concentration of 10 mM and the potassium chloride or the potassium acetate is at a concentration of 50 mM.

In a preferred embodiment of the method for replicating, amplifying or sequencing of the invention, the polyoxyethylenated sorbitan monolaurate is in a proportion between 0.01% and 0.03% of the total volume, the ammonium chloride is at a concentration between 80 mM and 100 mM, the buffer tris-hydrochloric, tris-acetic or HEPES is at a concentration between 30 mM and 45 mM and at a pH between 7.2 and 8.0, the magnesium chloride is at a concentration between 5 mM and 15 mM and the potassium chloride or the potassium acetate is at a concentration between 40 mM and 60 mM.

In a more preferred embodiment of the method for replicating, amplifying or sequencing of the invention, the polyoxyethylenated sorbitan monolaurate is in a concentration of 0.025% of the total volume, the ammonium chloride is at a concentration of 90 mM, the buffer tris-hydrochloric, tris-acetic or HEPES is at a concentration of 40 mM and at a pH of 7.5, the magnesium chloride is at a concentration of 10 mM and the potassium chloride or the potassium acetate is at a concentration of 50 mM.

In a preferred embodiment of the method for replicating, amplifying or sequencing of the invention, the polyoxyethylenated sorbitan monolaurate is in a proportion between 0.01% and 0.03% of the total volume, the ammonium acetate is at a concentration between 80 mM and 100 mM, the buffer tris-hydrochloric, tris-acetic or HEPES is at a concentration between 30 mM and 45 mM and at a pH between 7.2 and 8.0, the magnesium chloride is at a concentration between 5 mM and 15 mM and the potassium chloride or the potassium acetate is at a concentration between 40 mM and 60 mM.

In a more preferred embodiment of the method for replicating, amplifying or sequencing of the invention, the polyoxyethylenated sorbitan monolaurate is in a concentration of 0.025% of the total volume, the ammonium acetate is at a concentration of 90 mM, the buffer tris-hydrochloric, tris-acetic or HEPES is at a concentration of 40 mM and at a pH of 7.5, the magnesium chloride is at a concentration of 10 mM and the potassium chloride or the potassium acetate is at a concentration of 50 mM.

As used in the present description, the term "replication" relates to the synthesis of a complementary DNA from a template DNA.

As used in the present description, the term "amplification" relates to the increase of the number of copies of a template DNA.

As used in the present description, the term "sequencing" relates to the determination of the order of the nucleotides of a template DNA.

"Contacting" is understood as the fact that the template DNA and the reaction mixture are incubated in primer extension conditions.

As used herein, the term "primer" relates to an oligonucleotide capable of acting as the starting point of the DNA synthesis when it is in primer extension conditions. Preferably, the primer is a deoxyribose oligonucleotide.

The primers can be prepared by means of any suitable method, including for example, but not limited to, the direct chemical synthesis. The primers can be designed to hybridize with specific deoxynucleotide sequences in the template DNA (specific primers) or can be randomly synthesized (arbitrary primers).

As used in the present description, the term "specific primer" relates to a primer the sequence of which is complementary to a specific deoxynucleotide sequence in the template DNA to be amplified.

"Complementary" is understood as the fact that the primer can be hybridized with a region of the template DNA such that it can act as the starting point of the DNA synthesis when it is in primer extension conditions. Preferably, that region has a 100% complementarity with a region of the template DNA. In other words, each nucleotide in the region of complementarity with the primer can form hydrogen bonds with a nucleotide present in the single stranded template. However, those with a normal experience in the field will acknowledge that primers having a region with less than 100% complementarity with respect to the template DNA will function to carry out the method for replicating, amplifying or sequencing of the present invention.

The term "arbitrary primer" relates to a primer the sequence of which is randomly synthesized and which is used to initiate the DNA synthesis in random positions of the template DNA. Generally, in the method for replicating, amplifying or sequencing of the present invention a population of arbitrary primers is used. The term "arbitrary primers"

relates to a set of primers with a random sequence and which are used to initiate the DNA synthesis in random positions of the template DNA.

In a preferred embodiment of the method for replicating, amplifying or sequencing of the invention, the primer is specific.

In another preferred embodiment of the method for replicating, amplifying or sequencing of the invention, the primer is arbitrary. Preferably, the arbitrary primer is protected against the action of 3"-5" exonucleases. And more preferably, the arbitrary primer is an oligonucleotide of 6 nucleotides, "hexanucleotide" or "hexamer" protected against the action of 3"-5" exonucleases.

As used in the present description, the expression "protected against the action of exonucleases" relates to a modified primer such that it is resistant to the nucleolytic degradation by any 3"-5" exonuclease activity present in the DNA polymerase chimera of the invention.

In the method for replicating, amplifying or sequencing of the invention, more than one primer can be used, being able to use specific and/or arbitrary primers.

In a preferred embodiment of the method for replicating, amplifying or sequencing of the invention, the primer is at a concentration between 2 μM and 100 μM. In a more preferred embodiment, the primer is at a concentration between 20 μM and 80 μM. In a still more preferred embodiment, the primer is at a concentration between 40 μM and 60 μM. In a still more preferred embodiment, the primer is at a concentration of approximately 50 μM.

As used in the present description the term "nucleoside triphosphates" relates to organic molecules formed by the covalent bond of a pentose, a nitrogen base and three phosphate groups.

The term nucleoside triphosphates include deoxynucleoside triphosphates (dNTPs) such as for example, but not limited to dATP, dCTP, dITP, dUTP, dGTP, dTTP, or derivatives thereof. Preferably, the deoxynucleoside triphosphates are dATP, dTTP, dGTP and dCTP. Still more preferably, these four dNTPs are in equimolar conditions. In a preferred embodiment of this aspect of the invention, the deoxynucleoside triphosphates are at a concentration between 100 μM and 800 μM. In a more preferred embodiment, the deoxynucleoside triphosphates are at a concentration between 200 μM and 600 μM. In a still more preferred embodiment, the deoxynucleoside triphosphates are at a concentration of approximately 500 μM.

The term nucleoside triphosphates also includes dideoxynucleoside triphosphates (ddNTPs) such as for example, but not limited to, ddATP, ddCTP, ddITP, ddUTP, ddGTP, ddTTP, or derivatives thereof.

In some preferred embodiments of the method for replicating, amplifying or sequencing of the invention, at least one nucleoside triphosphate or one primer is labelled by means of techniques well known in the state of the art. The nucleotide labelled can be, for example, a deoxynucleoside triphosphate or a dideoxynucleoside triphosphate. Detectable labels include, for example, radioactive isotopes, fluorescent labels, chemiluminescent labels, bioluminescent labels or enzymatic labels.

As used in the present description, the term "template DNA" relates to a DNA molecule that can serve as a substrate for synthesizing a complementary DNA strand; i.e., it relates to a DNA molecule to be replicated, amplified or sequenced. In a preferred embodiment the template DNA is plasmid DNA. In another preferred embodiment, the template DNA is genomic DNA.

Replicating, amplifying or sequencing of the template DNA is carried out in primer extension conditions. The expression "primer extension conditions" refers to the conditions in which the template DNA-dependent synthesis initiated in a primer can take place.

The template DNA synthesis according to the method for replicating, amplifying or sequencing of the present invention can take place by means of a thermal cycling process or at an essentially constant temperature.

"Isothermal conditions" is understood as essentially constant temperature. Preferably, the template DNA synthesis according to the method for replicating, amplifying or sequencing of the present invention takes place at an essentially constant temperature. More preferably, at an essentially constant temperature between 25 and 40° C., and still more preferably at approximately 30° C.

A large number of methods allowing DNA amplification are known in the state of the art. Some methods require a thermal cycling process such as, for example, but not limited to the polymerase chain reaction (PCR). Other methods do not require a thermal cycling process, rather they are performed at a essentially constant temperature such as, for example, but not limited to the rolling circle amplification (RCA), the multiple detachment amplification (MDA), the strand displacement amplification (SDA) or the loop mediated amplification (LAMP). The amplification of a template DNA according to the method of the present invention can take place by means of a thermal cycling process or at an essentially constant temperature.

Preferably, the amplification of the template DNA according to the method for amplifying of the present invention takes place by means of rolling circle amplification (RCA), by means of multiple detachment amplification (MDA), strand displacement amplification (SDA) or loop mediated amplification (LAMPA).

Another aspect of the present invention relates to a kit or device comprising elements suitable for carrying out the method for replicating, amplifying or sequencing of the present invention.

Another aspect of the present invention relates to a kit for carrying out the method for replicating, amplifying or sequencing of the present invention comprising:
 a) the DNA polymerase chimera of the invention,
 b) a buffer, and
 c) magnesium chloride.

In a preferred embodiment of this aspect of the invention, the kit further comprises polyoxyethylenated sorbitan monolaurate, an ammonium salt, a potassium salt or a combination of any the above.

Preferably, said ammonium salt is selected from the list comprising: ammonium sulfate, ammonium chloride or ammonium acetate.

Preferably, said potassium salt is potassium chloride or potassium acetate.

In a preferred embodiment of this aspect of the invention, the kit further comprises a primer. In a more preferred embodiment, the primer is an arbitrary primer which is protected against the action of 3"-5" exonucleases.

In a preferred embodiment of this aspect of the invention, the kit further comprises nucleoside triphosphates. For example, in a more preferred embodiment of this aspect of the invention, the kit further comprises deoxynucleoside triphosphates and/or a dideoxynucleoside triphosphate.

In a preferred embodiment of this aspect of the invention, the kit comprises at least one triphosphate nucleoside or one labelled primer. The labelled nucleoside can be, for example, a deoxynucleoside triphosphate or a dideoxynucleoside triphosphate.

The kit can further include, without any form of limitation, buffers, agents to prevent contamination, etc. On the other hand, the kit can include all the supports and recipients necessary for putting it into practice and for its optimization. Preferably, the kit further comprises the instructions for carrying out the method of the invention.

Throughout the description and claims, the word "comprises" and its variants do not exclude other technical features, additives, components or steps. For the persons skilled in the art, other objects, advantages and features of the invention will be inferred in part from the description and in part from the practice of the invention. The following drawings and examples are provided by way of illustration and do not limit the present invention.

EXAMPLES

The following specific examples provided in this patent document serve to illustrate the nature of the present invention. These examples are only included for illustrative purposes and must not be interpreted as limitations to the invention claimed herein. Therefore, the examples described below illustrate the invention without limiting the field of application thereof.

Example 1

Optimization of the Experimental Conditions for Amplifying DNA with Multiple Priming by the φ29 DNA Polymerase It has been shown that the φ29 DNA polymerase amplifies $10^4$-$10^6$ times starting from several picograms of circular DNA. For this purpose a reaction buffer containing 40 mM tris-HCl, pH 7.5, 50 mM KCl and 10 mM $MgCl_2$ (hereinafter Buffer A) was used. After testing the influence of different detergent and salt conditions on the DNA amplification capacity of the DNA polymerase of φ29, it is found that the simultaneous addition of 0.025% Tween® 20 and 45 mM $(NH_4)_2SO_4$ to the Buffer A highly improve the amplification of the limited amounts of provided DNA.

Reaction conditions for amplifying plasmid DNA.—The incubation mixture contained 12.5 µl of buffer A, 50 µM of hexamers protected against the action of the 3"-5" exonuclease, 500 µM of each of the deoxynucleoside triphosphates (dCTP, dGTP, dTTP and dATP), the indicated amounts of a plasmid DNA (with a size of 4.2 kbp) and, where indicated, $(NH_4)_2SO_4$ 45 mM or 0.025% Tween® 20 or a combination of both was added. The DNA was denatured by incubation at 95° C. for 3 minutes and subsequent cooling in ice for 5 min. The reaction was initiated upon adding 50 nM φ29 DNA polymerase and it was stopped after the incubation at 30° C. by means of heating to 65° C. for 10 min. To analyze the results, 1 µl samples were taken from the reactions, the amplified DNA was digested with the EcoRI restriction endonuclease and was subjected to electrophoresis in 0.7% agarose gel. The DNA was detected by means of staining the gels with ethidium bromide.

Reaction conditions for amplifying genomic DNA.—The incubation mixture contained 12.5 µl of buffer A, 45 mM $(NH_4)_2SO_4$, 0.025% Tween® 20, 50 µM of hexamers protected against the action of the 3"-5" exonuclease, 500 µM of each of the deoxynucleoside triphosphates (dCTP, dGTP, dTTP and dATP) and the indicated amounts of *Bacillus subtilis* genomic DNA (with a size of 4 Mpb). The DNA denatured by incubation at 95° C. for 3 minutes and subsequent cooling in ice for 5 min. The reaction was initiated upon adding 50 nM φ29 DNA polymerase and it was stopped after the incubation at 30° C. by means of heating to 65° C. for 10 min. To analyze the results, 1 µl samples were taken from the reactions and were subjected to electrophoresis in 0.7% agarose gel. The DNA was detected by means of staining the gels with ethidium bromide.

FIG. 1 shows the effect of adding 45 mM (NH4)2SO4 and 0.025% Tween® 20 in the amplification of small amounts of provided plasmid DNA. As shown, the φ29 DNA polymerase did not give any amplification product detectable with the standard Buffer A when 100 fg of provided DNA were used. In these reaction conditions, the addition of 0.025% Tween® 20 in the absence of DNA caused the appearance of trace DNA products, most probably as a consequence of the nonspecific DNA amplification caused by the hybridization and elongation of the random hexamer primers. The same trace was observed with 10 fg of provided DNA. However, in the presence of 100 fg of provided DNA, the addition of 0.025% Tween® 20 allowed the φ29 DNA polymerase to produce a detectable amount of amplified plasmid. The total production of specific or nonspecific amplified DNA indicates that the addition of 0.025% Tween® 20 to the Buffer A powers the amplification capacity of the φ29 DNA polymerase. A similar effect was observed with the NP40 detergent. Contrarily, other analyzed detergents such as Triton X100 and Triton X114 did not power the amplification capacity of the φ29 DNA polymerase (not shown). The simultaneous addition of 0.025% Tween® 20 and 45 mM (NH4)2SO4 to the buffer A has two consequences in the yield and the specificity of the amplified products: 1) DNA amplification in the absence of provided DNA was not detected; 2) several µg of plasmid DNA of unit length were obtained by amplification even when the provided amount of DNA was as low as 10 fg. As control, the addition of 45 mM (NH4)2SO4 to the Buffer A did not produce any improvement in the amplification capacity of the φ29 DNA polymerase.

Figure 2:
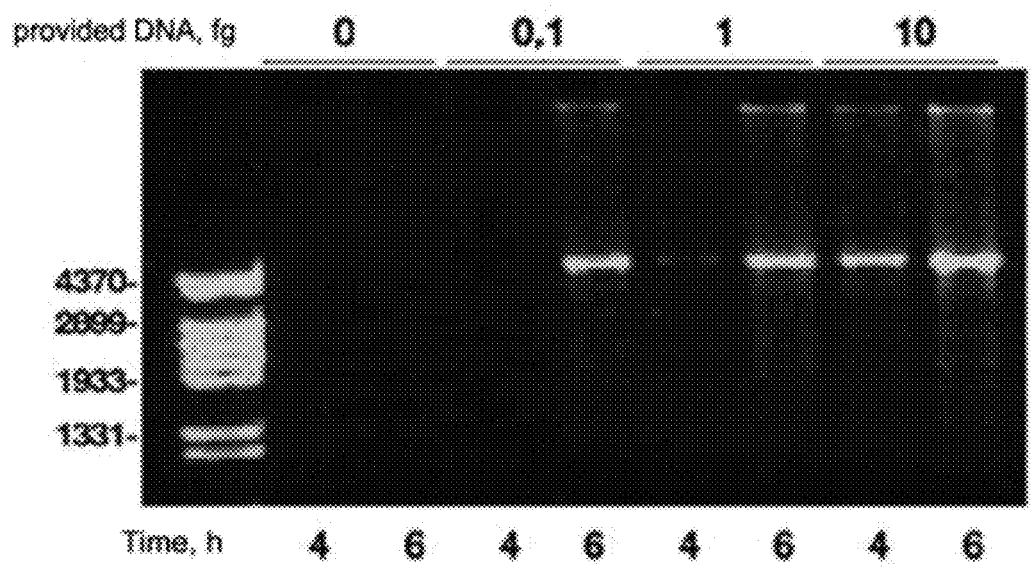
FIG. 2 shows the amplification of different amounts of plasmid DNA (in the order of femtograms) by the φ29 DNA polymerase in the presence of Tween® 20 and (NH4)2SO4. The assay was carried out as described in the main text in the presence of 0.025% Tween® 20 and of 45 mM (NH4)2SO4. The DNA length markers are the same as those used in FIG. 1.

Therefore, it can be concluded that the simultaneous addition of 0.025% Tween® 20 and 45 mM (NH4)2SO4 to the Buffer A (hereinafter Buffer B) produces a clear optimization of the experimental conditions for carrying out the amplification with multiple priming of circular DNA by the φ29 DNA polymerase, both being absolutely necessary reactants to amplify limited amounts (10 fg) of provided DNA. In fact, as can be seen in FIG. 2, the use of Buffer B allowed the φ29 DNA polymerase to synthesize micrograms of DNA by using a provided amount of plasmid as low as 0.1 fg (~24 molecules) after 6 hours of reaction. As quality control, the digestion of the amplification products with EcoRI generated linear dsDNA fragments of 4.2 kb which indicated that the amplification products were really tandem repeats of the original plasmid. Again, the Buffer B also prevented the non-specific DNA amplification (see FIG. 2 the lanes corresponding to the reactions carried out without provided DNA).

Figure 3:
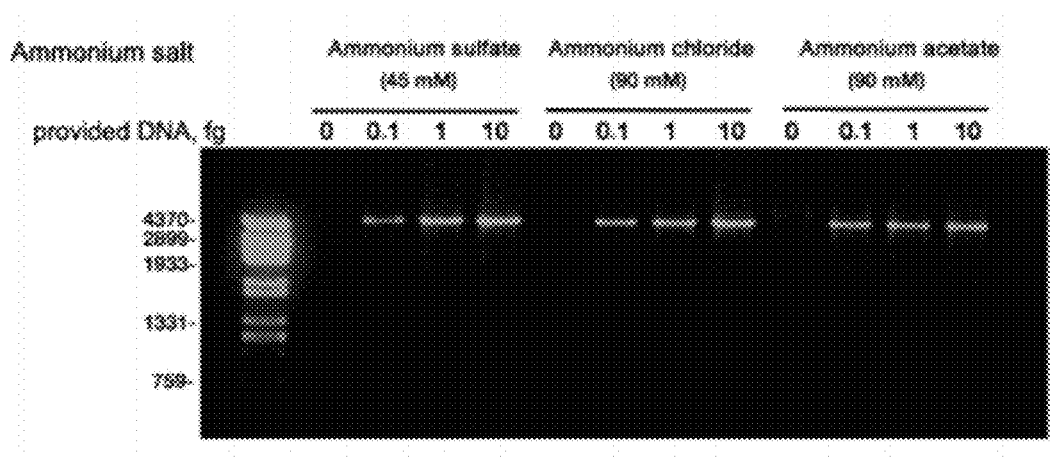
FIG. 3 shows the effect of the NH4+ ion in the amplification capacity of the φ29 DNA polymerase. The assay was carried out as described in the main text in the presence of 0.025% Tween® 20 and the indicated ammonium salt as well as the indicated amounts of plasmid DNA (4.2 kpb). After incubating at 30° C. for 6 h, the reactions were analyzed as described in the main text. The DNA length markers are the same as those used in FIG. 1.

FIG. 3 shows the effect of the ammonium ions and 0.025% Tween® 20 in improving the amplification of small amounts of plasmid DNA. The assay was carried out in the previously mentioned conditions in the presence of 0.025% Tween® 20 and the indicated ammonium salt. As can be observed in FIG. 3 both the NH4Cl and the NH4CH3COO had a similar effect to the (NH4)2SO4 both in the yield and in the specificity of the amplified products. This result indicates that the aforementioned effect of the (NH4)2SO4 in the amplification of limiting amounts of plasmid DNA is due to the NH4+ ions.

Figure 4:
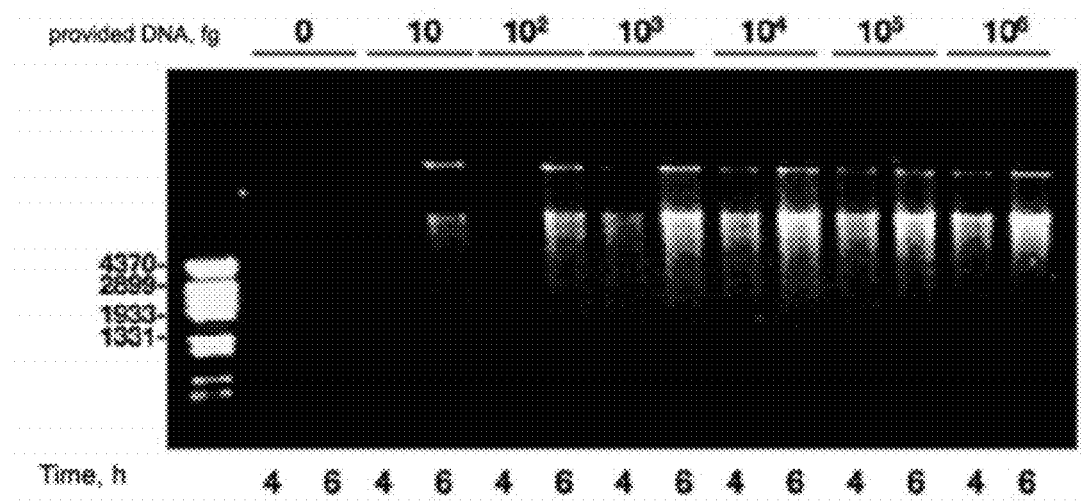
FIG. 4 shows the amplification of different amounts of Bacillus subtilis genomic DNA by the φ29 DNA polymerase in the presence of Tween® 20 and (NH4)2SO4. The assay was carried out as described in the main text in the presence of 0.025% Tween® 20 and 45 mM (NH4)2SO4. The DNA length markers are the same as those used in FIG. 1.

To determine if the optimized conditions described above was also applied to the amplification of genomic DNA, the same type of assays performed in the presence of limited concentrations of *B. subtilis* genomic DNA (4 Mpb in length) was carried out. As shown in FIG. 4, the presence of 0.025% Tween® 20 and 45 mM (NH4)2SO4 in the buffer B, on the one hand prevented the nonspecific DNA amplification (lanes without provided DNA), and on the other hand, allowed the φ29 DNA polymerase to give detectable and specific genomic DNA amplification even when 10 fg of provided DNA were used, i.e., an amount 106 times lower than that recommended in the current commercial genomic amplification kits.

Figure 5:
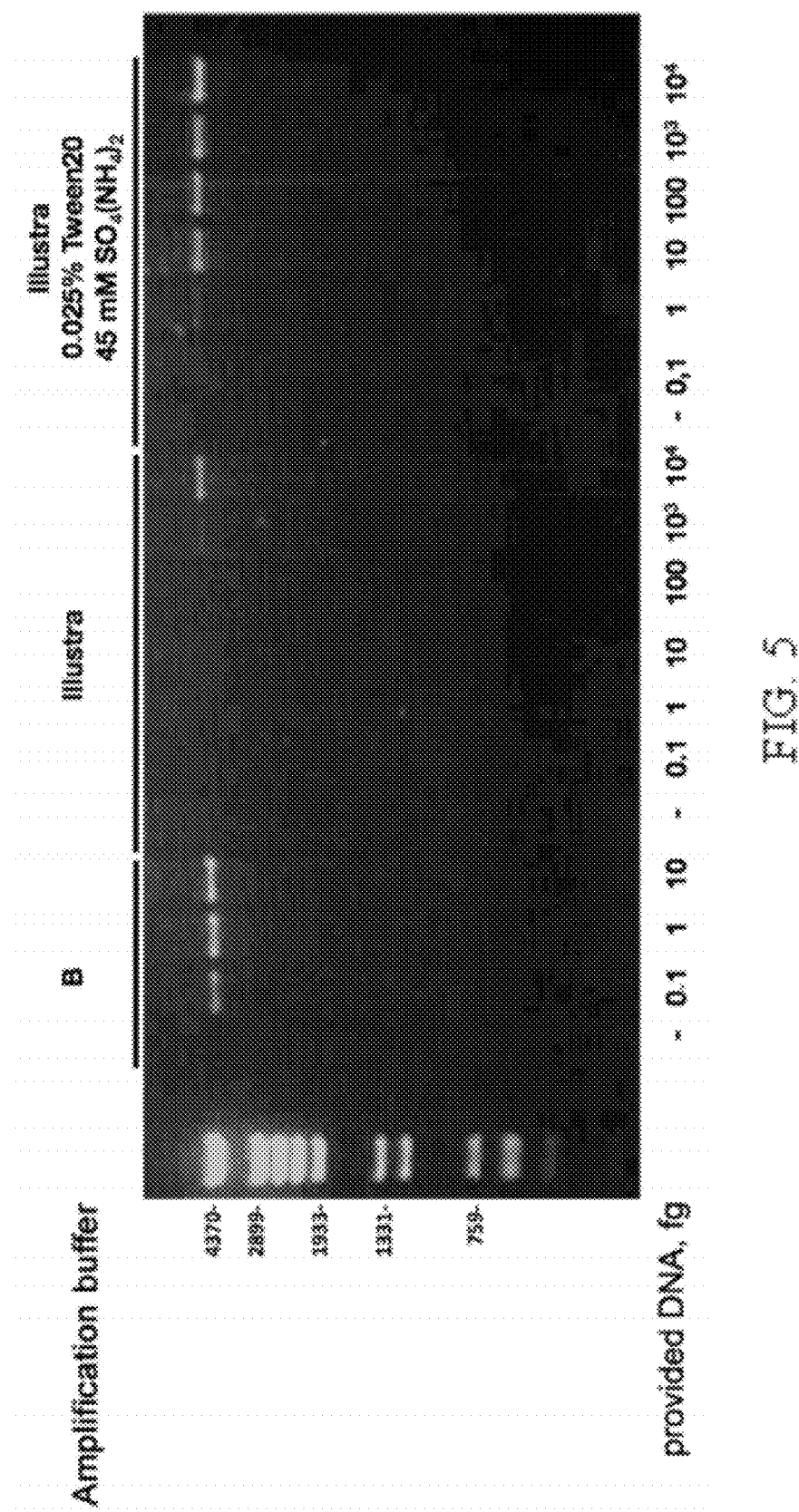
FIG. 5 shows the significant improvement depicted by the addition of 0.025% Tween® 20 and 45 mM (NH4)2SO4 to the current reaction buffer of a commercial kit for the amplification of DNA based on the ø29 DNA polymerase (Illustra kit of General Electrics HealthCare). The assay was carried out as described in the main text. The DNA length markers are the same as those used in FIG. 1.

To determine if the simultaneous addition of 0.025% Tween® 20 and 45 mM (NH4)2SO4 increases the amplification efficiency of the current commercial kits for amplifying DNA based on the φ29 DNA polymerase, the same type of plasmid DNA amplification assays described in FIGS. 1, 2 and 3 was carried out. FIG. 5 shows the significant improvements depicted by the addition of 0.025% Tween® 20 and 45 mM (NH4)2SO4 to the current reaction buffer of the Illustra kit (GE HealthCare). As can be observed, by following the recommendation of the supplier, with the Illustra kit only amounts of plasmid provided equal to or greater than 10 pg can be amplified in a detectable manner in agarose gel. Contrarily, the simultaneous addition of 0.025% Tween® 20 and 45 mM (NH4)2SO4 to the reaction buffer of the Illustra kit significantly reduces the needed amount of DNA which can be amplified, amplification products from provided 1 fg of plasmid DNA being observed, involving an improvement of four orders of magnitude in the amplification.

Example 2

Figure 6:
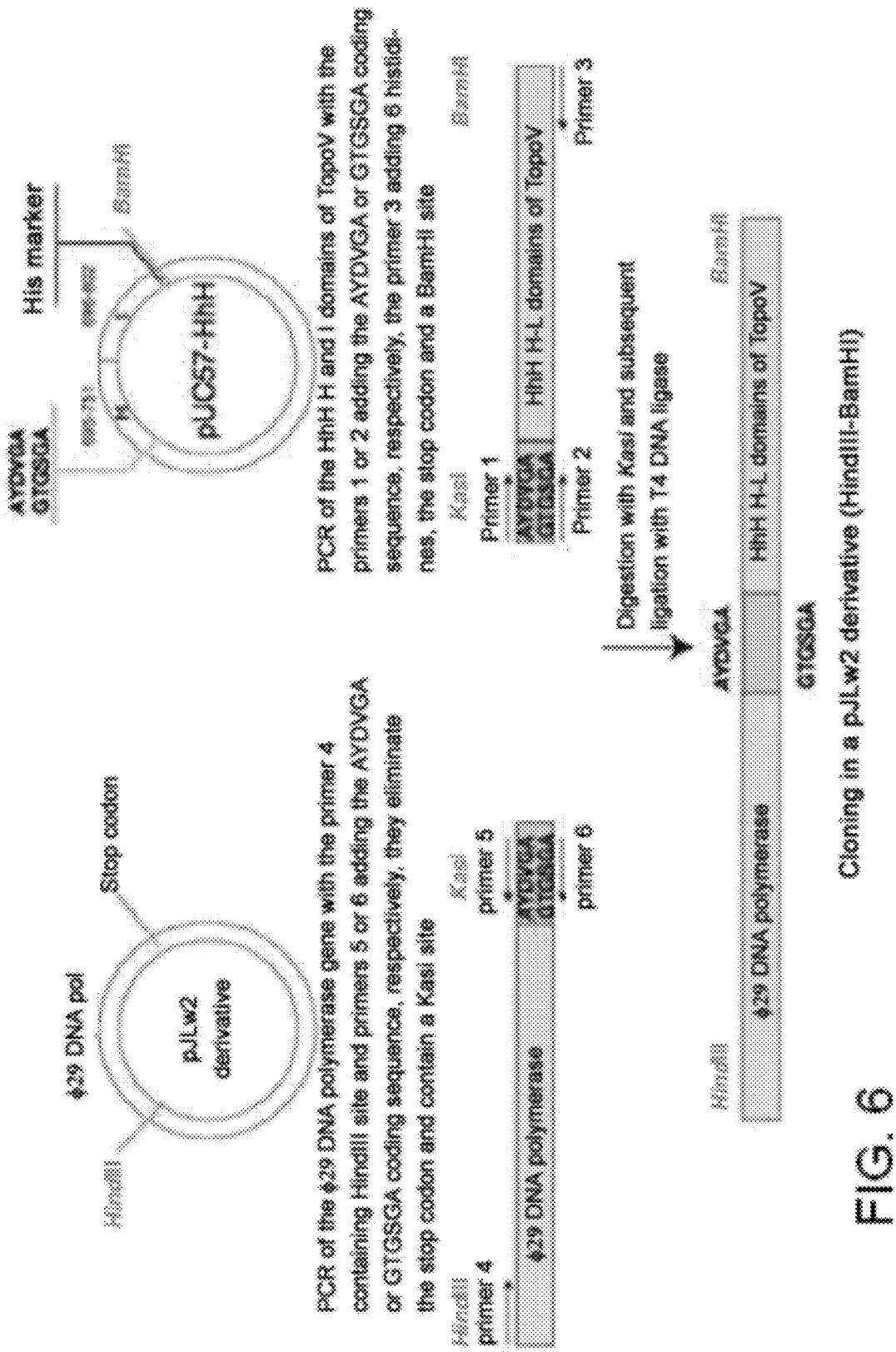
FIG. 6 shows a diagram of the different steps followed to construct the chimeras HAY, HGT, HIAY and HIGT (SEQ ID NO: 5 [AYDVGA] and SEQ ID NO: 6 [GTGSGA]).

Improvement of the Amplification Capacity of the φ29 DNA Polymerase by the Addition of HhH Domains φ29 DNA polymerase was fused with one or two HhH domains to construct new DNA polymerases with an improved DNA binding capacity which allows using less amounts of provided DNA. The inspection of the structure of the φ29 DNA polymerase lead to selecting the fusion of the HhH domains with the C-terminal end of the enzyme since this end (the end of the subdomain thumb) is close to the tunnel entrance of the top dsDNA sequence. The fusion of the HhH domains with the N-terminal end of the φ29 DNA polymerase would compromise the intrinsic capacity of strand detachment since the biochemical and structural data demonstrated that the unwinding of the parent DNA takes place near the amino end. Furthermore, positioning the HhH domains in the N-terminal end would not be suitable one for improving the binding of the dsDNA part formed by hybridization of the hexamer primer with the template DNA. In this sense, the fusion of a sequence $(His)_6$ at the N-terminal end of the φ29 DNA polymerase has a damaging effect in the amplification.
2.1 Chimeric DNA Polymerase Construct To make the chimeras HIAY and HIGT, GenScript Corporation was entrusted to synthesise a DNA fragment which contained the nucleotides encoding the HhH domains, H (56 amino acids) and I (51 amino acids) of the topoisomerase V of *M. kandleri* (code in GenBank AF311944 and (Pavlov et al. Proc Natl Acad Sci USA. 2002; 99: 13510-13515), and the latter was cloned between the EcoRV sites of the commercial vector pUC57. The resulting plasmid pUC57-HhH was used as template for amplifying a DNA fragment encoding the domains H and I by PCR. Therefore, the primer 3 (SEQ ID NO: 7) together with the primers 1 (SEQ ID NO: 8) or 2 (SEQ ID NO: 9) gave the DNA I and II fragments of 369 bp, respectively. In addition to a KasI site introduced by both primers, primer 1 also introduced the sequence encoding the SEQ ID NO: 5 connector (Pavlov et al. Proc Natl Acad Sci USA. 2002; 99: 13510-13515), whereas the primer 2 introduced the nucleotide sequence encoding the SEQ ID NO: 6 connector (a SEQ ID NO: 10 connector derivative previously described in Sun et al. Proteins. 2006; 65: 231-238). The primer 3 contained the sequence encoding the 6 histidine residues followed by a stop codon and a BamHI site (see in FIG. 6 a simplified diagram of the chimeric DNA polymerase construct).

At the same time, a pJLw2 plasmid derivative (Lázaro et al. Methods Enzymol. 1995; 262: 42-49) containing the gene encoding the φ29 DNA polymerase (572 amino acids) was used as a template for a PCR reaction carried out with the primer 4 (SEQ ID NO: 11) including a 5' HindIII site and the primers 5 (SEQ ID NO: 12) or 6 (SEQ ID NO: 13), to obtain the fragments III and IV of 1757 bp, respectively. The fragments III and IV will therefore contain the DNA encoding the φ29 DNA polymerase followed by the SEQ ID NO: 5 (Fragment III) and SEQ ID NO: 6 (fragment IV) sequences which also include a KasI site. The fragments I-IV were purified in 0.7% agarose gels and were then digested with KasI. The digested DNA fragments I and III, and II and IV were ligated with the T4 DNA ligase to obtain a linear DNA of 2108 bp encoding the chimera HIAY (Fragment V) and HIGT (Fragment VI), respectively. The ligated products were purified in 0.7% agarose gels and were then digested with the BamHI and HindIII endonucleases. The digested products were purified by electrophoresis in agarose gels. The fragments V and VI were finally cloned in the vector pT7-4 (Tabor et al. Proc Natl Acad Sci USA. 1985; 82: 1074-1078). The chimeras HIAY (φ29 DNA polymerase+SEQ ID NO: 5 connector+ domains H and I of topoV) and HIGT (φ29 DNA polymerase+SEQ ID NO: 6 connector+domains H and I of topoV) were used as the template to construct the chimeras HGT and HAY, respectively, by inserting a stop codon after the H fragment of TopoV by means of the QuikChange® (Stratagene) directed mutagenesis kit. The confirmation of the DNA sequence and the absence of additional mutations was carried out by means of sequencing the entire gene. The chimeric DNA polymerases were expressed in BL21(DE3) cells of *E. coli* which housed the cloned chimeric gene in a pJLw2 plasmid derivative, and were then essentially purified as described in (Lázaro et al. Methods Enzymol. 1995; 262: 42-49).

In summary, the chimeric DNA polymerases obtained were the following:
HAY: φ29 DNA polymerase—SEQ ID NO: 5—HhH H (635 aa; ~73 kDa)
HGT: φ29 DNA polymerase—SEQ ID NO: 6—HhH H (635 aa; ~73 kDa))
HIAY: φ29 DNA polymerase—SEQ ID NO: 5—HhH H—I (692 aa; ~80 kDa)
HIGT: φ29 DNA polymerase—SEQ ID NO: 6—HhH H—I (692 aa; ~80 kDa)
2.2. DNA Binding Capacity of the Chimeric DNA Polymerases.

To determine if the fusion of the HhH motifs at the end of the φ29 DNA polymerase conferred an improved binding capacity of the chimeras to the DNA, the retardation analysis of the electrophoretic mobility of the DNA in gel was carried out.

Conditions of the assay.—The oligonucleotides of 15 bases (SEQ ID NO: 14) and 21 bases (SEQ ID NO: 15) having a 5' extension of six nucleotides in addition to the sequence complementary to the oligonucleotide of 15 bases were supplied by Isogen. The oligonucleotide of 15 bases was labelled in 5' with [γ-32P] ATP and the T4 kinase polynucleotide. The oligonucleotide of 15 bases labelled in 5' was hybridized with that of 21 bases in the presence of 0.2 M NaCl and 60 mM (pH 7.5) tris-HCl. The hybridized oligonucleotide molecule of 15 bases labelled in 5'/oligonucleotide of 21 bases was used to analyze the interaction with the natural or chimeric φ29 DNA polymerases. The incubation mixture, in a final volume of 20 μl contained 50 mM (pH 7.5) tris-HCl, 1 mM dithiothreitol, 10 mM MgCl2, 20 mM ammonium sulfate, 0.1 mg/ml bovine serum albumin (BSA), 4% glycerol, 1 nM oligonucleotide molecule of 15 bases/21 bases, and the indicated concentration of the natural or chimeric φ29 DNA polymerase. After incubation for 5 min at 4° C., the samples were subjected to electrophoresis in 4% polyacrylamide gels (w/v) (monomer: bis 80:1) which contained 12 mM (pH 7.5) tris-acetate and 1 mM EDTA and were developed at 4° C. in the same buffer at 8 V/cm, essentially as described by (Carthew et al. Cell. 1985; 43: 439-448). After autoradiography, the polymerase-dsDNA complex was detected as a detachment of the mobility (retardation) in the migration position of the labelled DNA.

Figure 7:
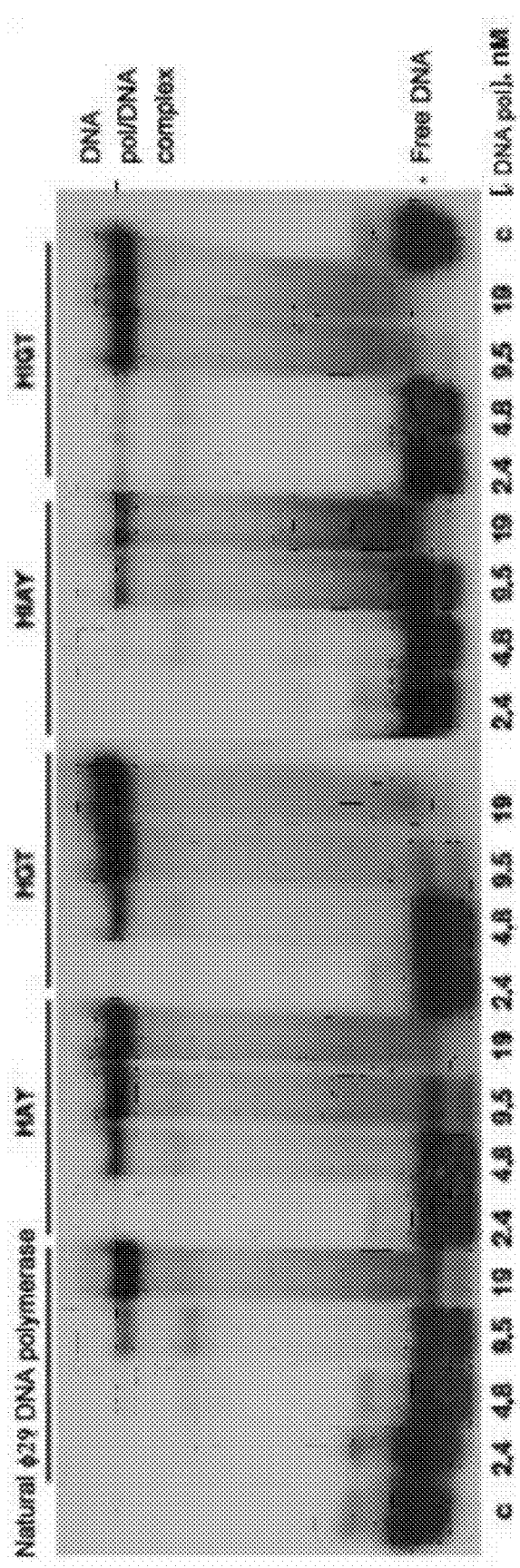
FIG. 7 shows the retardation in gel of the primer/template DNA molecules by the natural and chimeric φ29 DNA polymerases. The hybridized molecule of 15 bases/21 bases labelled in 5' (dsDNA) was incubated with natural φ29 DNA polymerase or with the chimeric DNA polymerase indicated in the conditions described in the text. The mobilities of the free dsDNA and of the polymerase-DNA complex were detected by autoradiography after the separation thereof by electrophoresis in 4% (w/v) native polyacrylamide gels (80:1 monomer:bisacrylamide).

In these conditions, the natural φ29 DNA polymerase produces a single retardation band using the labelled hybridized oligonucleotide molecule of 15 bases/21 bases (see FIG. 7) which has been interpreted as a stable enzyme-DNA complex competent for polymerization (Mendez et al. J Biol Chem. 1994; 269: 30030-30038). The chimeras HAY, HGT and HIGT showed a DNA binding capacity greater than the natural enzyme since the larger part of the substrate was detached with a 9.5 nM concentration unlike the natural DNA polymerase which needed an approximately 2 times higher concentration. The chimera HIAY had a DNA binding capacity similar to, or even less than, that of the natural polymerase. From these results, it can be concluded that, in general, the addition of the HhH H and H+I domains of Topo V to the C-terminal end of the φ29 DNA polymerase confers an improved DNA binding capacity, although there are exceptions such as in the case of the chimera HIAY.

2.3. Rolling Circle Replication by the Chimeric DNA Polymerases.

To determine if the improvement in the DNA binding obtained by the addition of the HhH domains of the TopoV to the C-terminal end of the φ29 DNA polymerase affected, on the one hand, the polymerization activity, and on the other, the processive synthesis of DNA coupled to the strand detachment, replication assays with M13 primer in which the DNA polymerase starts the polymerization from the 3'-OH group of a DNA oligonucleotide were carried out. In this assay, the first replication cycle does not require strand detachment, but once it is completed, the polymerase finds the 5' end of the primer, thus requiring an active detachment to continue the following replication cycles (rolling circle type).

Conditions of the assay.—The M13mp18 ssDNA was hybridized with the universal primer in the presence of 0.2 M NaCl and 60 mM (pH 7.5) tris-HCl, and the resulting molecule was used as a primer/template to analyze the polymerization of processive DNA coupled to the strand detachment by the chimeric DNA polymerases. The incubation mixture contained in 25 μl, 50 mM (pH 7.5) tris-HCl, 10 mM MgCl2, 1 mM dithiothreitol, 4% glycerol, 0.1 mg/ml BSA, 40 μM dCTP, dGTP, dTTP, and [α-32P]dATP (1 μCi), 250 ng M13mp18 ssDNA primed with the oligonucleotide of sequence SEQ ID NO: 16, and 30 nM natural or chimeric φ29 DNA polymerase. After incubating for the indicated times at 30° C., the reactions were stopped by the addition of 0.1% EDTA 10 mM-SDS, and the samples were filtered through Sephadex G-50 columns. The relative activity was calculated from the Cerenkov radiation corresponding to the excluded volume. For size analysis, the labelled DNA was denatured by treatment with 0.7 M NaOH and was subjected to electrophoresis in 0.7% alkaline agarose gels as described in (McDonell et al. J Mol Biol. 1977; 110: 119-146). After the electrophoresis, the M13mp8 ssDNA of unit in length was detected by staining with ethidium bromide, and the gels were then dried and autoradiographed.

Figure 8:
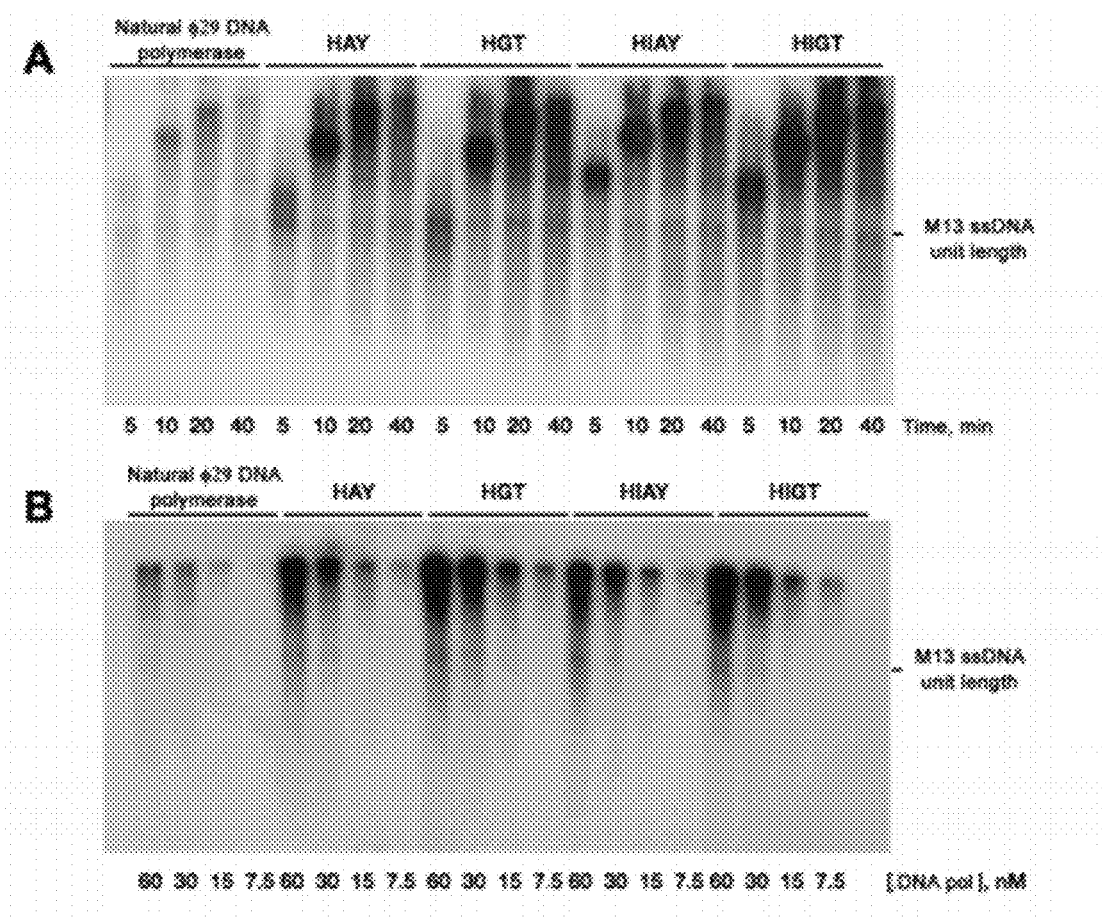
FIG. 8 shows the processive replication of DNA by the natural and chimeric φ29 DNA polymerases. (A) Replication of M13 DNA coupled to strand detachment by the natural and chimeric φ29 DNA polymerases. The replication of 250 ng of M13 DNA with a single primer was carried out as has been described in the text using natural or chimeric φ29 DNA polymerases (30 nM). The position of the M13 DNA of unit in length is shown on the right. (B) Processive synthesis by the natural and chimeric φ29 DNA polymerases. The assay was carried out in the same conditions as in (A), using decreasing concentrations of the DNA polymerase indicated. After incubating at 30° C. for 20 min, the samples were processed as has been described in (A).

As shown in FIG. 8A, a significant discovery is that the presence of the HhH domains does not interfere with the strand detachment capacity of the chimeric DNA polymerases. The amount of DNA synthesized by the chimeras HAY, HGT, HIAY and HIGT was greater than that synthesized by the natural φ29 DNA polymerase (4, 5, 5 and 7 times, respectively). The replication speed was similar (in the case of the chimeras HAY and HGT) or even faster (chimeras HIGT and HIAY) than that obtained with the natural φ29 DNA polymerase. This result indicates that the presence of HhH domains in the C-terminal end of the φ29 DNA polymerase in the chimeras improves the use of the template DNA during the rolling circle replication.

2.4. Processive Polymerization by the Chimeric DNA Polymerases.

φ29 DNA polymerase is a paradigm for the processive DNA replication since it is capable of incorporating more than 70 kb without dissociating from the DNA in the absence of auxiliary proteins. Therefore, whether the fusion of the HhH domains in the C-terminal end of the φ29 DNA polymerase in the chimeric DNA polymerases affected the processivity of the polymerization was analyzed.

Conditions of the assay.—The processivity of the chimeric DNA polymerases was analyzed with different proportions of enzyme/DNA. The incubation mixture contained, in 25 μl, 50 mM (pH 7.5) tris-HCL, 10 mM MgCl2, 1 mM ditiothreitol, 4% glycerol, 0.1 mg/ml BSA, 40 μM dCTP, dGTP, dTTP, and [α-32P]dATP (1 μCi), 250 ng primed M13mp18 ssDNA, and the indicated decreasing amounts of the natural φ29 DNA polymerase or chimeric DNA polymerases. After incubating for 20 min at 30° C., the reactions were stopped by the addition of 10 mM EDTA −0.1% SDS, and the samples were filtered through Sephadex G-50 columns. For size analysis, the labelled DNA was denatured by treatment with 0.7 M NaOH and was subjected to electrophoresis in 0.7% alkaline agarose gel. The processivity of the polymerization was evaluated by analyzing the length of the replication products with decreasing proportions of DNA polymerase/DNA.

As shown in FIG. 8B, decreasing proportions of enzyme/DNA did not alter the length of the elongation products synthesized by the natural or chimeric φ29 DNA polymerases, according to a processive DNA polymerization model.

2.5. Rolling Circle Amplification (RCA) with Multiple Priming of Plasmid DNA by the Natural and Chimeric φ29 DNA Polymerases.

As has been described above, both the high processivity and the strand detachment capacity which the φ29 DNA polymerase has were the base for the development of one of the more efficient processes for amplifying isothermal ssDNA by Amersham Biosciences/Molecular Staging, in which the φ29 DNA polymerase combined with random hexamer primers achieves the isothermal and accurate amplification of 104 to 106 times by strand detachment of picograms of circular plasmids [Templiphi™ (www.gehealthcare.com)]. The results with a φ29 DNA polymerase which contained a $(His)_6$ sequence fused in the C-terminal end thereof showed that, despite the efficiency thereof, during the rolling circle replication with a single primer, it was incapable of giving amplification products detectable during the RCA with multiple priming. The same was certain for other mutant derivatives of the φ29 DNA polymerase which showed greater affinity for the dNTP, replicating the M13 DNA at the level of the natural DNA polymerase, but could not give amplification products. Therefore, although the fusion of HhH domains to the C-terminal end of the φ29 DNA polymerase improved the intrinsic capacity of the natural enzyme to perform the rolling circle replication with a single primer, a similar efficiency increase during the RCA with multiple priming could not be anticipated.

Conditions of the assay.—The incubation mixture contained, in 12.5 µl of buffer B, 10 fg plasmid DNA (4.2 kpb) as supply. To denature the DNA provided, the samples were incubated for 3 min at 95° C. and were then cooled in ice for 5 min. The reactions were initiated by the addition of 50 nM natural or chimeric φ29 DNA polymerase. After incubating at 30° C. for the indicated times, the reactions were stopped by incubating the samples for 10 min at 65° C. 1 µl of each reaction was digested with EcoRI and was then analyzed by electrophoresis in 0.7% agarose gel. After electrophoresis, the amplified DNA was detected by staining with ethidium bromide.

Figure 9:
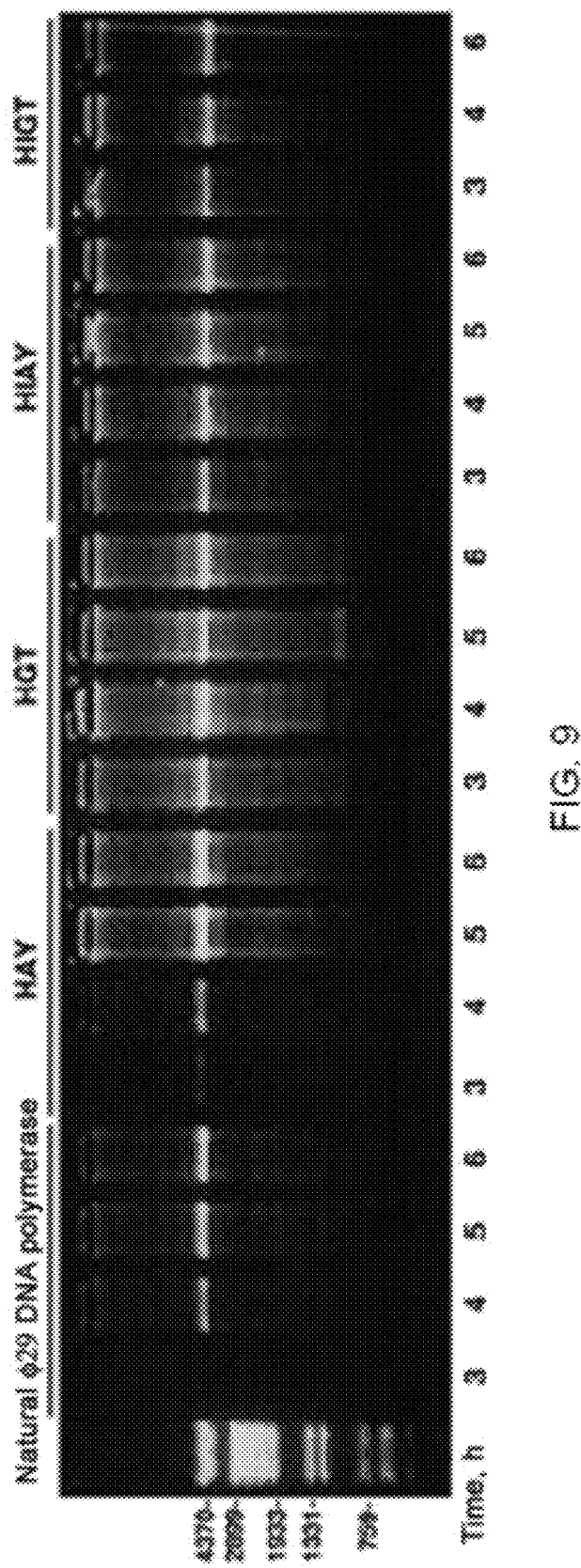
FIG. 9 shows the rolling circle amplification with multiple priming of 10 fg plasmid DNA by the natural and chimeric φ29 DNA polymerases. The assay was carried out as described in the main text in the presence of buffer B and 50 nM of the DNA polymerase indicated. The DNA length markers are the same as those used in FIG. 1.

As shown in FIG. 9, the natural φ29 DNA polymerase gave a detectable amplification product from 4 h of reaction. The chimera HAY gave a detectable amplification product from 4 h, the total production amount of amplification after 5 h being twice of that obtained with the natural φ29 DNA polymerase. The chimera HGT produced an amount of amplified DNA comparable to that obtained with the chimera HAY; it is interesting that the yield of maximum amplification was obtained in the shorter reaction time (3 h). The maximum amount of amplified DNA with the chimeras HIAY and HIGT was similar to that obtained with the natural φ29 DNA polymerase, although as in the case of the chimera HGT, said maximum yield was achieved from 3 h of reaction. After digesting the synthesized DNA with the four chimeras with EcoRI, more than 80% of the amplified DNA gave a dsDNA fragment of 4.2 kb which indicated that the large part of the amplification product really consisted of tandem repeats of the original plasmid.

This result indicates a greater capacity of the chimeric DNA polymerases to amplify limited amounts (10 fg) of the plasmid DNA than the natural φ29 DNA polymerase.

2.6 Amplification of the DNA with Multiple Priming of Genomic DNA by the Natural and Chimeric φ29 DNA Polymerases.

In addition to the RCA technology with multiple priming described above, a process for amplifying entire genome known as multiple displacement amplification (MDA) was developed based on the properties of the φ29 DNA polymerase combined with the use of random hexamer primers (Dean et al. Proc Natl Acad Sci USA. 2002; 99: 5261-5266). The Genomiphi™ (GE Healthcare) and Repli-G® (Qiagen) kits, based on this process, require a minimum amount of 10 ng of genomic DNA. To investigate if the chimeric DNA polymerases have improved capacity for amplifying limited amounts of genomic DNA with respect to the natural φ29 DNA polymerase, MDA of the *B. subtilis* genomic DNA was performed.

Conditions of the assay.—The incubation mixture contained, in 12.5 µl of buffer B, 100 fg *B. subtilis* genomic DNA. To denature the DNA, the samples were incubated for 3 min at 95° C. and were then cooled with ice for 5 min. The reactions were initiated by the addition of 50 nM natural or chimeric φ29 DNA polymerase. After incubating at 30° C. for the indicated times, the reactions were stopped by incubating the samples for 10 min at 65° C. 1 µl of each reaction was analyzed by electrophoresis in 0.7% agarose gel. After electrophoresis, the amplified DNA was detected by staining with ethidium bromide.

Figure 10:
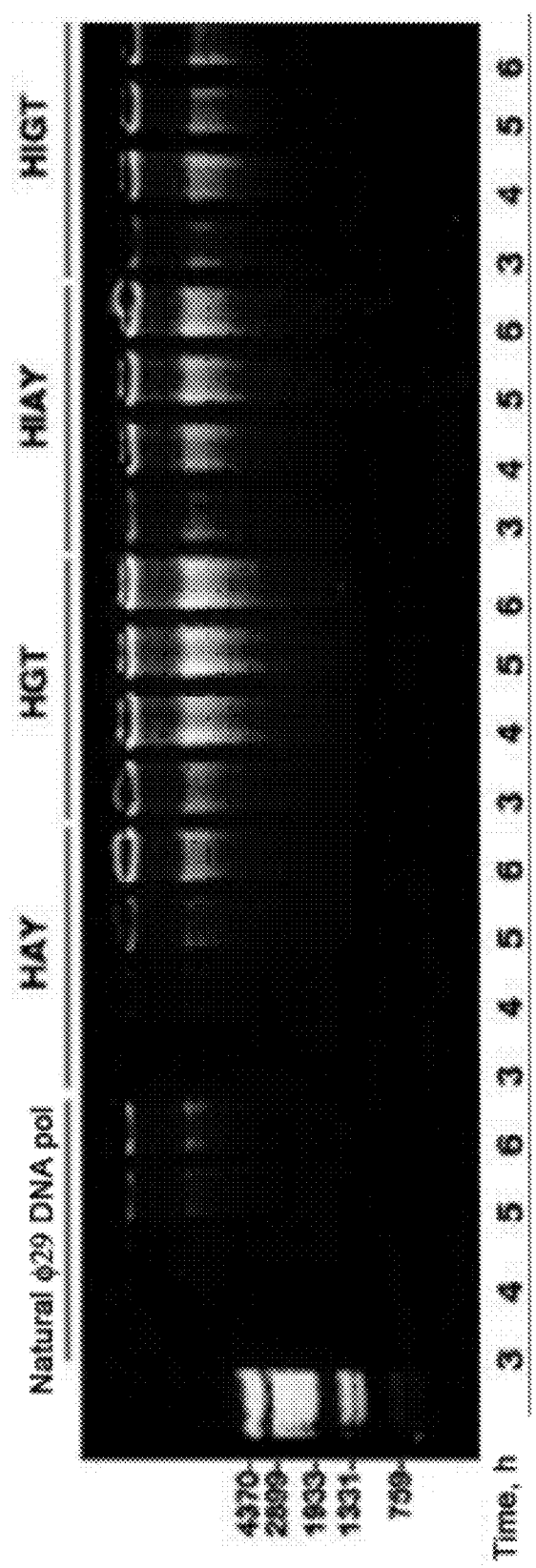
FIG. 10 shows the amplification of the entire genome with multiple priming of 100 fg B. subtilis genomic DNA with natural and chimeric φ29 DNA polymerases. The assay was carried out as described in the text in the presence of buffer B and 50 nM of the DNA polymerase indicated. The DNA length markers are the same as those used in FIG. 1.

As shown in FIG. 10, in the experimental conditions described above, the natural φ29 DNA polymerase gave detectable amplification products after 5 h of incubation. The chimera HAY also produced amplification products in this time, but the total amount of amplified DNA after 6 h was much greater than that obtained with the natural φ29 DNA polymerase. As can also be observed, the rest of the chimeras, HGT, HIAY and HIGT gave clear amplification products in the shorter assay time (3 h), the total amplified amount in this time being similar to (HIAY and HIGT) or much greater (HGT) than that observed after 6 h with the natural φ29 DNA polymerase. These results indicate that the presence of the HhH domains provides the chimeric DNA polymerases an improved capacity for amplifying the genomic DNA with respect to the natural φ29 DNA polymerase.

2.7 Measurement of the Accuracy of the Chimeric DNA Polymerases.

3 µl of each of the samples from the experiment showed in FIG. 9, corresponding to the multiple rolling circle amplification of 10 fg plasmid DNA were incubated in the presence of 17 µl of the restriction mixture (2 µl New England Biolabs (NEB) 10×EcoRI Buffer, 0.5 µl [10 units] of the NEB EcoRI endonuclease and 14.5 µl H₂O) to obtain linear monomers of the amplified plasmid. After incubating for 1 hour at 37° C., the DNA was purified through Qiagen Gel-Extraction Kit Columns and was eluted in 30 µl TE buffer (10 mM (pH 7.5) tris-HCl, 1 mM EDTA). 10 µl of each elution were religated by incubating them with 2 µl NEB 10× Ligase Buffer, 8 µl H2O and 0.5 µl (200 units) NEB T4 DNA ligase. The reactions were incubated for one night at 16° C., and *E. coli* XL-1 Blue competent cells were transformed with 2 µl of each. Approximately 1000 transformants were obtained with each of the amplification samples, whereas none were obtained with the control samples which contained 10 fg of a plasmid of 4.2 kpb treated in the same manner as each of the samples described above. Two clones were selected from each transformation and the corresponding plasmids were purified and sequenced according to standard processes. The oligonucleotides used for the sequencing were: pT7-N (SEQ ID NO: 17), sp4+10 (SEQ ID NO: 18) and sp10+7 (SEQ ID NO: 19). In total, 4918 non-overlapping nucleotides of each of the plasmids amplified by the natural and chimeric DNA polymerases were sequenced. The results are shown in Table 1 and they indicate a synthesis accuracy of the chimeric DNA polymerases similar to the natural enzyme.

TABLE 1

Polymerization accuracy of the natural and chimeric φ29 DNA polymerases

| Polymerase | Mutations |
|---|---|
| Natural | 0 |
| HAY | 0 |
| HGT | 0 |
| HIAY | 1 (transversion G to T) |
| HIGT | 0 |

4918 non-overlapping nucleotides of each of the plasmids amplified by the natural and chimeric DNA polymerases were sequenced as described in the main text.

The foregoing description and examples have been set forth merely to illustrate the invention and are not intended to be limiting. Since modifications of the described embodi-

The invention claimed is:

1. A DNA polymerase chimera comprising:
   a) a phi29 (φ29) DNA polymerase having at least 80% sequence identity to the amino acid sequence as set forth in SEQ ID NO: 1, covalently attached at its C-terminal end directly to
   b) the amino acid sequence as set forth in SEQ ID NO: 5 or SEQ ID NO: 6, covalently attached at its C-terminal end directly to
   c) the helix-hairpin-helix (HhH) domain as set forth in SEQ ID NO: 3, wherein said DNA polymerase chimera has DNA polymerase activity.

2. The DNA polymerase chimera according to claim 1, wherein the amino acid sequence of (c) further comprises at least one HhH domain of a protein covalently attached at its C-terminal end, which is selected from the list comprising:
   topoisomerase V of Methanopyrus kandleri,
   Mut Y, Nth, MutM/Fpg, Nei, UvrC, DinP, RecR, UmuC, DnaE or DnlJ of *Escherichia coli*,
   RAD1, RAD2, RAD10, RAD27, RAD55, RAD57, REV1, OGG1, NTG1, NTG2, DIN-7 or EXO-1 of yeasts, or
   a homologous protein of the above in *Bacillus subtilis, Caenorhabditis elegans, Haemophilus influenzae, Methanococcus jannaschii, Micrococcus luteus, Methanobacterium thermoformicum* or *Salmonella typhimurium*.

3. The DNA polymerase chimera according to claim 1, wherein the amino acid sequence of (c) further comprises at least one HhH domain derived from the topoisomerase V of *Methanopyrus kandleri* covalently attached at its C-terminal end.

4. The DNA polymerase chimera according to claim 3, wherein the amino acid sequence of (c) is SEQ ID NO: 3 covalently attached at its C-terminal end directly to SEQ ID NO: 4.

5. The DNA polymerase chimera according to claim 1, wherein the φ29 type DNA polymerase of (a) has an amino acid sequence having an identity of at least 90% with SEQ ID NO: 1.

6. The DNA polymerase chimera according to claim 5, wherein the φ29 type DNA polymerase of (a) has the amino acid sequence SEQ ID NO: 1.

7. The DNA polymerase chimera according to claim 1, wherein the φ29 type DNA polymerase of (a) has a modification in the exonuclease domain and wherein said modified DNA polymerase has less than 10% of exonuclease activity than the corresponding naturally occurring DNA polymerase.

8. The DNA polymerase chimera according to claim 7, wherein the modified φ29 type DNA polymerase of (a) has less than 1% of exonuclease activity than the corresponding naturally occurring DNA polymerase.

9. The DNA polymerase chimera according to claim 8, wherein the modified φ29 type DNA polymerase of (a) lacks detectable exonuclease activity with respect to the corresponding naturally occurring DNA polymerase.

10. A kit for replicating, amplifying or sequencing a template DNA comprising:
    a) a DNA polymerase chimera comprising,
       (i) a phi29(φ29) DNA polymerase having at least 80% sequence identity to the amino acid sequence as set forth in SEQ ID NO: 1, covalently attached at its C-terminal end directly to
       (ii) the amino acid sequence as set forth in SEQ ID NO: 5 or SEQ ID NO: 6, covalently attached at its C-terminal end directly to
       (iii) the helix-hairpin-helix (HhH) domain as set forth in SEQ ID NO: 3, wherein said DNA polymerase chimera has DNA polymerase activity,
    b) a buffer, and
    c) magnesium chloride.

11. The kit according to claim 10, further comprising polyoxyethylenated sorbitan monolaurate.

12. The kit according to claim 10, further comprising an ammonium salt.

13. The kit according to claim 10, further comprising a potassium salt.

14. The kit according to claim 10, further comprising a primer.

15. The kit according to claim 14, wherein the primer is arbitrary and is protected against the action of exonucleases.

16. The kit according to claim 10, further comprising nucleoside triphosphates.

17. The kit according to claim 14, wherein at least one nucleoside triphosphate or one primer is labelled.

* * * * *

SEQUENCE LISTING

<160> NUMBER OF SEQ ID NOS: 19

<210> SEQ ID NO 1
<211> LENGTH: 572
<212> TYPE: PRT
<213> ORGANISM: Bacteriophage phi-29

<400> SEQUENCE: 1

Met Pro Arg Lys Met Tyr Ser Cys Asp Phe Glu Thr Thr Thr Lys Val
1               5                   10                  15

Glu Asp Cys Arg Val Trp Ala Tyr Gly Tyr Met Asn Ile Glu Asp His
            20                  25                  30

Ser Glu Tyr Lys Ile Gly Asn Ser Leu Asp Glu Phe Met Ala Trp Val
        35                  40                  45

Leu Lys Val Gln Ala Asp Leu Tyr Phe His Asn Leu Lys Phe Asp Gly
    50                  55                  60

Ala Phe Ile Ile Asn Trp Leu Glu Arg Asn Gly Phe Lys Trp Ser Ala
65                  70                  75                  80

Asp Gly Leu Pro Asn Thr Tyr Asn Thr Ile Ile Ser Arg Met Gly Gln
                85                  90                  95

Trp Tyr Met Ile Asp Ile Cys Leu Gly Tyr Lys Gly Lys Arg Lys Ile
            100                 105                 110

His Thr Val Ile Tyr Asp Ser Leu Lys Lys Leu Pro Phe Pro Val Lys
        115                 120                 125

Lys Ile Ala Lys Asp Phe Lys Leu Thr Val Leu Lys Gly Asp Ile Asp
    130                 135                 140

Tyr His Lys Glu Arg Pro Val Gly Tyr Lys Ile Thr Pro Glu Glu Tyr
145                 150                 155                 160

Ala Tyr Ile Lys Asn Asp Ile Gln Ile Ile Ala Glu Arg Leu Leu Ile
                165                 170                 175

Gln Phe Lys Gln Gly Leu Asp Arg Met Thr Ala Gly Ser Asp Ser Leu
            180                 185                 190

Lys Gly Phe Lys Asp Ile Ile Thr Thr Lys Lys Phe Lys Lys Val Phe
        195                 200                 205

Pro Thr Leu Ser Leu Gly Leu Asp Lys Glu Val Arg Tyr Ala Tyr Arg
    210                 215                 220

Gly Gly Phe Thr Trp Leu Asn Asp Arg Phe Lys Glu Lys Glu Ile Gly
225                 230                 235                 240

Glu Gly Met Val Phe Asp Val Asn Ser Leu Tyr Pro Ala Gln Met Tyr
                245                 250                 255

Ser Arg Leu Leu Pro Tyr Gly Glu Pro Ile Val Phe Glu Gly Lys Tyr
            260                 265                 270

Val Trp Asp Glu Asp Tyr Pro Leu His Ile Gln His Ile Arg Cys Glu
        275                 280                 285

Phe Glu Leu Lys Glu Gly Tyr Ile Pro Thr Ile Gln Ile Lys Arg Ser
    290                 295                 300

Arg Phe Tyr Lys Gly Asn Glu Tyr Leu Lys Ser Ser Gly Gly Glu Ile
305                 310                 315                 320

Ala Asp Leu Trp Leu Ser Asn Val Asp Leu Glu Leu Met Lys Glu His
                325                 330                 335

Tyr Asp Leu Tyr Asn Val Glu Tyr Ile Ser Gly Leu Lys Phe Lys Ala
            340                 345                 350

Thr Thr Gly Leu Phe Lys Asp Phe Ile Asp Lys Trp Thr Tyr Ile Lys
            355                 360                 365

Thr Thr Ser Glu Gly Ala Ile Lys Gln Leu Ala Lys Leu Met Leu Asn
    370                 375                 380

Ser Leu Tyr Gly Lys Phe Ala Ser Asn Pro Asp Val Thr Gly Lys Val
385                 390                 395                 400

Pro Tyr Leu Lys Glu Asn Gly Ala Leu Gly Phe Arg Leu Gly Glu Glu
            405                 410                 415

Glu Thr Lys Asp Pro Val Tyr Thr Pro Met Gly Val Phe Ile Thr Ala
            420                 425                 430

Trp Ala Arg Tyr Thr Thr Ile Thr Ala Ala Gln Ala Cys Tyr Asp Arg
            435                 440                 445

Ile Ile Tyr Cys Asp Thr Asp Ser Ile His Leu Thr Gly Thr Glu Ile
            450                 455                 460

Pro Asp Val Ile Lys Asp Ile Val Asp Pro Lys Lys Leu Gly Tyr Trp
465                 470                 475                 480

Ala His Glu Ser Thr Phe Lys Arg Val Lys Tyr Leu Arg Gln Lys Thr
            485                 490                 495

Tyr Ile Gln Asp Ile Tyr Met Lys Glu Val Asp Gly Lys Leu Val Glu
            500                 505                 510

Gly Ser Pro Asp Asp Tyr Thr Asp Ile Lys Phe Ser Val Lys Cys Ala
            515                 520                 525

Gly Met Thr Asp Lys Ile Lys Lys Glu Val Thr Phe Glu Asn Phe Lys
            530                 535                 540

Val Gly Phe Ser Arg Lys Met Lys Pro Lys Pro Val Gln Val Pro Gly
545                 550                 555                 560

Gly Val Val Leu Val Asp Asp Thr Phe Thr Ile Lys
            565                 570

<210> SEQ ID NO 2
<211> LENGTH: 984
<212> TYPE: PRT
<213> ORGANISM: Methanopyrus kandleri

<400> SEQUENCE: 2

Met Ala Leu Val Tyr Asp Ala Glu Phe Val Gly Ser Glu Arg Glu Phe
1               5                   10                  15

Glu Glu Glu Arg Glu Thr Phe Leu Lys Gly Val Lys Ala Tyr Asp Gly
            20                  25                  30

Val Leu Ala Thr Arg Tyr Leu Met Glu Arg Ser Ser Ala Lys Asn
        35                  40                  45

Asp Glu Glu Leu Leu Glu Leu His Gln Asn Phe Ile Leu Leu Thr Gly
    50                  55                  60

Ser Tyr Ala Cys Ser Ile Asp Pro Thr Glu Asp Arg Tyr Gln Asn Val
65                  70                  75                  80

Ile Val Arg Gly Val Asn Phe Asp Glu Arg Val Gln Arg Leu Ser Thr
                85                  90                  95

Gly Gly Ser Pro Ala Arg Tyr Ala Ile Val Tyr Arg Arg Gly Trp Arg
            100                 105                 110

Ala Ile Ala Lys Ala Leu Asp Ile Asp Glu Glu Asp Val Pro Ala Ile
        115                 120                 125

Glu Val Arg Ala Val Lys Arg Asn Pro Leu Gln Pro Ala Leu Tyr Arg
    130                 135                 140

Ile Leu Val Arg Tyr Gly Arg Val Asp Leu Met Pro Val Thr Val Asp
145                 150                 155                 160

```
Glu Val Pro Pro Glu Met Ala Gly Glu Phe Glu Arg Leu Ile Glu Arg
                165                 170                 175
Tyr Asp Val Pro Ile Asp Glu Lys Glu Glu Arg Ile Leu Glu Ile Leu
            180                 185                 190
Arg Glu Asn Pro Trp Thr Pro His Asp Glu Ile Ala Arg Arg Leu Gly
        195                 200                 205
Leu Ser Val Ser Glu Val Glu Gly Glu Lys Asp Pro Glu Ser Ser Gly
    210                 215                 220
Ile Tyr Ser Leu Trp Ser Arg Val Val Asn Ile Glu Tyr Asp Glu
225                 230                 235                 240
Arg Thr Ala Lys Arg His Val Lys Arg Arg Asp Arg Leu Leu Glu Glu
                245                 250                 255
Leu Tyr Glu His Leu Glu Glu Leu Ser Glu Arg Tyr Leu Arg His Pro
            260                 265                 270
Leu Thr Arg Arg Trp Ile Val Glu His Lys Arg Asp Ile Met Arg Arg
        275                 280                 285
Tyr Leu Glu Gln Arg Ile Val Glu Cys Ala Leu Lys Leu Gln Asp Arg
    290                 295                 300
Tyr Gly Ile Arg Glu Asp Val Ala Leu Cys Leu Ala Arg Ala Phe Asp
305                 310                 315                 320
Gly Ser Ile Ser Met Ile Ala Thr Thr Pro Tyr Arg Thr Leu Lys Asp
                325                 330                 335
Val Cys Pro Asp Leu Thr Leu Glu Glu Ala Lys Ser Val Asn Arg Thr
            340                 345                 350
Leu Ala Thr Leu Ile Asp Glu His Gly Leu Ser Pro Asp Ala Ala Asp
        355                 360                 365
Glu Leu Ile Glu His Phe Glu Ser Ile Ala Gly Ile Leu Ala Thr Asp
    370                 375                 380
Leu Glu Glu Ile Glu Arg Met Tyr Glu Gly Arg Leu Ser Glu Glu
385                 390                 395                 400
Ala Tyr Arg Ala Ala Val Glu Ile Gln Leu Ala Glu Leu Thr Lys Lys
                405                 410                 415
Glu Gly Val Gly Arg Lys Thr Ala Glu Arg Leu Leu Arg Ala Phe Gly
            420                 425                 430
Asn Pro Glu Arg Val Lys Gln Leu Ala Arg Glu Phe Glu Ile Glu Lys
        435                 440                 445
Leu Ala Ser Val Glu Gly Val Gly Glu Arg Val Leu Arg Ser Leu Val
    450                 455                 460
Pro Gly Tyr Ala Ser Leu Ile Ser Ile Arg Gly Ile Asp Arg Glu Arg
465                 470                 475                 480
Ala Glu Arg Leu Leu Lys Lys Tyr Gly Gly Tyr Ser Lys Val Arg Glu
                485                 490                 495
Ala Gly Val Glu Glu Leu Arg Glu Asp Gly Leu Thr Asp Ala Gln Ile
            500                 505                 510
Arg Glu Leu Lys Gly Leu Lys Thr Leu Glu Ser Ile Val Gly Asp Leu
        515                 520                 525
Glu Lys Ala Asp Glu Leu Lys Arg Lys Tyr Gly Ser Ala Ser Ala Val
    530                 535                 540
Arg Arg Leu Pro Val Glu Glu Leu Arg Glu Leu Gly Phe Ser Asp Asp
545                 550                 555                 560
Glu Ile Ala Glu Ile Lys Gly Ile Pro Lys Lys Leu Arg Glu Ala Phe
                565                 570                 575
Asp Leu Glu Thr Ala Ala Glu Leu Tyr Glu Arg Tyr Gly Ser Leu Lys
```

```
                580             585             590
Glu Ile Gly Arg Arg Leu Ser Tyr Asp Asp Leu Leu Glu Leu Gly Ala
            595                 600             605

Thr Pro Lys Ala Ala Ala Glu Ile Lys Gly Pro Glu Phe Lys Phe Leu
    610                 615                 620

Leu Asn Ile Glu Gly Val Gly Pro Lys Leu Ala Glu Arg Ile Leu Glu
625                 630                 635                 640

Ala Val Asp Tyr Asp Leu Glu Arg Leu Ala Ser Leu Asn Pro Glu Glu
                645                 650                 655

Leu Ala Glu Lys Val Glu Gly Leu Gly Glu Glu Leu Ala Glu Arg Val
            660                 665                 670

Val Tyr Ala Ala Arg Glu Arg Val Glu Ser Arg Arg Lys Ser Gly Arg
        675                 680                 685

Gln Glu Arg Ser Glu Glu Trp Lys Glu Trp Leu Glu Arg Lys Val
    690                 695                 700

Gly Glu Gly Arg Ala Arg Arg Leu Ile Glu Tyr Phe Gly Ser Ala Gly
705                 710                 715                 720

Glu Val Gly Lys Leu Val Glu Asn Ala Glu Val Ser Lys Leu Leu Glu
                725                 730                 735

Val Pro Gly Ile Gly Asp Glu Ala Val Ala Arg Leu Val Pro Gly Tyr
            740                 745                 750

Lys Thr Leu Arg Asp Ala Gly Leu Thr Pro Ala Glu Ala Glu Arg Val
        755                 760                 765

Leu Lys Arg Tyr Gly Ser Val Ser Lys Val Gln Glu Gly Ala Thr Pro
    770                 775                 780

Asp Glu Leu Arg Glu Leu Gly Leu Gly Asp Ala Lys Ile Ala Arg Ile
785                 790                 795                 800

Leu Gly Leu Arg Ser Leu Val Asn Lys Arg Leu Asp Val Asp Thr Ala
                805                 810                 815

Tyr Glu Leu Lys Arg Arg Tyr Gly Ser Val Ser Ala Val Arg Lys Ala
            820                 825                 830

Pro Val Lys Glu Leu Arg Glu Leu Gly Leu Ser Asp Arg Lys Ile Ala
        835                 840                 845

Arg Ile Lys Gly Ile Pro Glu Thr Met Leu Gln Val Arg Gly Met Ser
    850                 855                 860

Val Glu Lys Ala Glu Arg Leu Leu Glu Arg Phe Asp Thr Trp Thr Lys
865                 870                 875                 880

Val Lys Glu Ala Pro Val Ser Glu Leu Val Arg Val Pro Gly Val Gly
                885                 890                 895

Leu Ser Leu Val Lys Glu Ile Lys Ala Gln Val Asp Pro Ala Trp Lys
            900                 905                 910

Ala Leu Leu Asp Val Lys Gly Val Ser Pro Glu Leu Ala Asp Arg Leu
        915                 920                 925

Val Glu Glu Leu Gly Ser Pro Tyr Arg Val Leu Thr Ala Lys Lys Ser
    930                 935                 940

Asp Leu Met Arg Val Glu Arg Val Gly Pro Lys Leu Ala Glu Arg Ile
945                 950                 955                 960

Arg Ala Ala Gly Lys Arg Tyr Val Glu Glu Arg Ser Arg Arg Glu
                965                 970                 975

Arg Ile Arg Arg Lys Leu Arg Gly
            980
```

<210> SEQ ID NO 3
<211> LENGTH: 56

```
<212> TYPE: PRT
<213> ORGANISM: Artificial Sequence
<220> FEATURE:
<223> OTHER INFORMATION: H domain of the topoisomerase V of Methanopyrus
      kandleri

<400> SEQUENCE: 3

Trp Lys Glu Trp Leu Glu Arg Lys Val Gly Glu Gly Arg Ala Arg Arg
1               5                   10                  15

Leu Ile Glu Tyr Phe Gly Ser Ala Gly Glu Val Gly Lys Leu Val Glu
            20                  25                  30

Asn Ala Glu Val Ser Lys Leu Leu Glu Val Pro Gly Ile Gly Asp Glu
        35                  40                  45

Ala Val Ala Arg Leu Val Pro Gly
    50                  55

<210> SEQ ID NO 4
<211> LENGTH: 51
<212> TYPE: PRT
<213> ORGANISM: Artificial Sequence
<220> FEATURE:
<223> OTHER INFORMATION: I domain of the topoisomerase V of Methanopyrus
      kandleri

<400> SEQUENCE: 4

Tyr Lys Thr Leu Arg Asp Ala Gly Leu Thr Pro Ala Glu Ala Glu Arg
1               5                   10                  15

Val Leu Lys Arg Tyr Gly Ser Val Ser Lys Val Gln Glu Gly Ala Thr
            20                  25                  30

Pro Asp Glu Leu Arg Glu Leu Gly Leu Gly Asp Ala Lys Ile Ala Arg
        35                  40                  45

Ile Leu Gly
    50

<210> SEQ ID NO 5
<211> LENGTH: 6
<212> TYPE: PRT
<213> ORGANISM: Artificial Sequence
<220> FEATURE:
<223> OTHER INFORMATION: synthetic amino acid sequence

<400> SEQUENCE: 5

Ala Tyr Asp Val Gly Ala
1               5

<210> SEQ ID NO 6
<211> LENGTH: 6
<212> TYPE: PRT
<213> ORGANISM: Artificial Sequence
<220> FEATURE:
<223> OTHER INFORMATION: synthetic amino acid sequence

<400> SEQUENCE: 6

Gly Thr Gly Ser Gly Ala
1               5

<210> SEQ ID NO 7
<211> LENGTH: 34
<212> TYPE: DNA
<213> ORGANISM: Artificial Sequence
<220> FEATURE:
<223> OTHER INFORMATION: primer 3

<400> SEQUENCE: 7
ggcgggatcc ttaatgatga tgatgatgat ggcc                              34
```

```
<210> SEQ ID NO 8
<211> LENGTH: 20
<212> TYPE: DNA
<213> ORGANISM: Artificial Sequence
<220> FEATURE:
<223> OTHER INFORMATION: primer 1

<400> SEQUENCE: 8
gcgtatgatg tgggcgccgg                                                   20

<210> SEQ ID NO 9
<211> LENGTH: 38
<212> TYPE: DNA
<213> ORGANISM: Artificial Sequence
<220> FEATURE:
<223> OTHER INFORMATION: primer 2

<400> SEQUENCE: 9
ggcaccggct ctggcgcctg gaaagaatgg ctggaacg                               38

<210> SEQ ID NO 10
<211> LENGTH: 6
<212> TYPE: PRT
<213> ORGANISM: Artificial Sequence
<220> FEATURE:
<223> OTHER INFORMATION: synthetic amino acid sequence

<400> SEQUENCE: 10

Gly Thr Gly Ser Gly Ala
1               5

<210> SEQ ID NO 11
<211> LENGTH: 22
<212> TYPE: DNA
<213> ORGANISM: Artificial Sequence
<220> FEATURE:
<223> OTHER INFORMATION: primer 4

<400> SEQUENCE: 11
ccgtctccgg gagctgcatg tg                                                22

<210> SEQ ID NO 12
<211> LENGTH: 43
<212> TYPE: DNA
<213> ORGANISM: Artificial Sequence
<220> FEATURE:
<223> OTHER INFORMATION: primer 5

<400> SEQUENCE: 12
ggcgcccaca tcatacgctt tgattgtgaa tgtgtcatca acc                         43

<210> SEQ ID NO 13
<211> LENGTH: 43
<212> TYPE: DNA
<213> ORGANISM: Artificial Sequence
<220> FEATURE:
<223> OTHER INFORMATION: primer 6

<400> SEQUENCE: 13
ggcgccagag ccggtgcctt tgattgtgaa tgtgtcatca acc                         43
```

```
<210> SEQ ID NO 14
<211> LENGTH: 15
<212> TYPE: DNA
<213> ORGANISM: Artificial Sequence
<220> FEATURE:
<223> OTHER INFORMATION: 15 base pair oligonucleotide

<400> SEQUENCE: 14
gatcacagtg agtac                                                          15

<210> SEQ ID NO 15
<211> LENGTH: 21
<212> TYPE: DNA
<213> ORGANISM: Artificial Sequence
<220> FEATURE:
<223> OTHER INFORMATION: 21 base pair oligonucleotide

<400> SEQUENCE: 15
tctattgtac tcactgtgat c                                                   21

<210> SEQ ID NO 16
<211> LENGTH: 17
<212> TYPE: DNA
<213> ORGANISM: Artificial Sequence
<220> FEATURE:
<223> OTHER INFORMATION: primer

<400> SEQUENCE: 16
gttttcccag tcacgac                                                        17

<210> SEQ ID NO 17
<211> LENGTH: 22
<212> TYPE: DNA
<213> ORGANISM: Artificial Sequence
<220> FEATURE:
<223> OTHER INFORMATION: primer pT7-N

<400> SEQUENCE: 17
ccgtctccgg gagctgcatg tg                                                  22

<210> SEQ ID NO 18
<211> LENGTH: 26
<212> TYPE: DNA
<213> ORGANISM: Artificial Sequence
<220> FEATURE:
<223> OTHER INFORMATION: primer sp4+10

<400> SEQUENCE: 18
ccggatgaca gcaggcagtg acagtc                                              26

<210> SEQ ID NO 19
<211> LENGTH: 25
<212> TYPE: DNA
<213> ORGANISM: Artificial Sequence
<220> FEATURE:
<223> OTHER INFORMATION: primer sp10+7

<400> SEQUENCE: 19
ggtaagttag tagaaggtag tccag                                               25
```